United States Patent
Rouillon et al.

(10) Patent No.: US 11,099,193 B2
(45) Date of Patent: Aug. 24, 2021

(54) METHODS FOR DIAGNOSING OR MONITORING MUSCULAR DYSTROPHIES

(71) Applicant: GENETHON, Evry (FR)

(72) Inventors: Jeremy Rouillon, Corbeil-Essonnes (FR); Fedor Svinartchouk, Villejuif (FR); Jerome Poupiot, Bretigny sur Orge (FR); Isabelle Richard, Corbeil-Essonnes (FR)

(73) Assignee: GENETHON, Evry (FR)

( * ) Notice: Subject to any disclaimer, the term of this patent is extended or adjusted under 35 U.S.C. 154(b) by 291 days.

(21) Appl. No.: 15/110,868

(22) PCT Filed: Jan. 9, 2015

(86) PCT No.: PCT/EP2015/050372
§ 371 (c)(1),
(2) Date: Jul. 11, 2016

(87) PCT Pub. No.: WO2015/104403
PCT Pub. Date: Jul. 16, 2015

(65) Prior Publication Data
US 2016/0334417 A1    Nov. 17, 2016

(30) Foreign Application Priority Data
Jan. 9, 2014 (EP) .................................. 14305029

(51) Int. Cl.
*G01N 31/00* (2006.01)
*G01N 33/53* (2006.01)
*G01N 33/68* (2006.01)

(52) U.S. Cl.
CPC . *G01N 33/6887* (2013.01); *G01N 2800/2878* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| 6,103,466 | A  | * | 8/2000 | Grobet | ................. | C07K 14/495 |
|---|---|---|---|---|---|---|
|  |  |  |  |  |  | 435/6.11 |
| 9,546,112 | B2 | * | 1/2017 | Voit | ................... | A61K 38/1709 |
| 9,933,438 | B2 | * | 4/2018 | Rouillon | ............ | G01N 33/6887 |

FOREIGN PATENT DOCUMENTS

CA        2836750 A1 *  6/2015  ........... G01N 33/483

OTHER PUBLICATIONS

Schoenauer et al. (J Mol. Biol. 2008, vol. 376, pp. 338-351).*
Koebis et al. (Genes to Cells, 2011, vol. 16. pp. 961-972).*
Brown et al. (Journal of Bioanalysis & Biomedicine, 2012, S7, pp. 1-8).*
Mizuno et al. (PLoS ONE, Mar. 2011, vol. 6, No. 3, e18388, pp. 1-6).*
Nadarajah et al. (Neuromuscular Disorders, vol. 21,2011, pp. 569-578).*
Schoenauer et al. (J Mol. Biol. 2008, vol. 376, pp. 338-351) (Year: 2008).*
Brown et al. (Journal of Bioanalysis & Biomedicine, 2012, S7, pp. 1-8) (Year: 2012).*
Nadarajah et al. (Neuromuscular Disorders, vol. 21,2011, pp. 569-578). (Year: 2011).*
Koebis, M. et al. "Alternative splicing of myomesin 1 gene is aberrantly regulated in myotonic dystrophy type 1" *Genes to Cells*, 2011, pp. 961-972, vol. 16.
Mizuno, H. et al. "Identification of Muscle-Specific MicroRNAs in Serum of Muscular Dystrophy Animal Models: Promising Novel Blood-Based Markers for Muscular Dystrophy" *PLoS ONE*, Mar. 30, 2011, pp. 1-6, e18388, vol. 6, No. 3.
Schoenauer, R. et al. "Myomesin 3, a Novel Structural Component of the M-band in Striated Muscle" *Journal of Molecular Biology*, Nov. 22, 2007, pp. 338-351, vol. 376, No. 2.
Xu, J. et al. "Functional Analysis of Slow Myosin Heavy Chain 1 and Myomesin-3 in Sarcomere Organization in Zebrafish Embryonic Slow Muscles" *Journal of Genetics and Genomics*, Jan. 11, 2012, pp. 69-80, vol. 39, No. 2.
Written Opinion in International Application No. PCT/EP2015/050372, dated Mar. 30, 2015, pp. 1-4.

* cited by examiner

*Primary Examiner* — Lisa V Cook
(74) *Attorney, Agent, or Firm* — Saliwanchik, Lloyd & Eisenschenk

(57) ABSTRACT

The invention relates to a method for prognosing, diagnosing, determining the risk, and monitoring the evolution of a muscular dystrophy. It also relates to a method for evaluating the efficacy of a treatment of a muscular dystrophy in a subject in need thereof.

Figure 1:
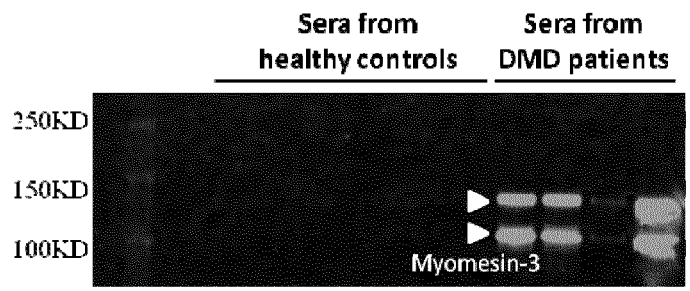

12 Claims, 16 Drawing Sheets
Specification includes a Sequence Listing.

| Sequence | Localisation | IonScore DMD 1 | IonScore DMD 2 | IonScore DMD 3 | IonScore DMD 4 |
|---|---|---|---|---|---|
| EQSTYVLVR | 355-363 | | | | 15 |
| DAEAENPGAPGSPLNVR | 364-380 | | | | 40 |
| ASELVVMGDHDAAR | 461-474 | | | | 34 |
| SVIGSGTWEAISSESPVR | 539-556 | 71 | | | 89 |
| FAVLDLEK | 560-567 | 23 | 29 | | 31 |
| AMNQYGLSDPSEPSEPIALR | 577-596 | | | | 58 |
| VGTSEWQTVNNKPIQGTR | 640-657 | 32 | | | 41 |
| QALATPSAPYGFALLNCGK | 695-713 | | | | 65 |
| VSDLHEGHFYEFR | 761-773 | | | | 32 |
| AANWAGVGELSAPSSLFECK | 776-795 | 30 | 17 | | 68 |
| LISGWNIDILER | 1008-1019 | | | | 34 |
| GSYTAQLQDGK | 1076-1086 | | | | 24 |
| VTEDCQVQLTCK | 1130-1141 | | | | 50 |
| IGALSATPLK | 1219-1228 | | | | 54 |
| QLSTDLSGQAFEDAMAEHQR | 1303-1322 | | | | 49 |

F

|     | KO_PBS / KO_1e11 | | KO_PBS / KO_5e11 | | KO_PBS / KO_1e12 | | KO_PBS / WT | | KO_1e11 / KO_5e11 | |
|-----|-------|-------|-------|-------|-------|-------|-------|-------|-------|-------|
|     | MYOM3 | CK | MYOM3 | CK | MYOM3 | CK | MYOM3 | CK | MYOM3 | CK |
| J0  | 0,193 | 0,338 | 0,616 | 0,436 | 0,459 | 0,210 | 0,000 | 0,003 | 0,253 | 0,229 |
| J14 | 0,409 | 0,709 | 0,003 | 0,022 | 0,003 | 0,031 | 0,002 | 0,028 | 0,000 | 0,046 |
| J28 | 0,023 | 0,147 | 0,000 | 0,025 | 0,000 | 0,008 | 0,000 | 0,012 | 0,001 | 0,116 |
| J42 | 0,009 | 0,394 | 0,000 | 0,013 | 0,000 | 0,011 | 0,000 | 0,009 | 0,001 | 0,000 |
| J56 | 0,010 | 0,061 | 0,002 | 0,029 | 0,002 | 0,022 | 0,002 | 0,020 | 0,001 | 0,032 |
| J70 | 0,002 | 0,695 | 0,001 | 0,082 | 0,000 | 0,054 | 0,000 | 0,046 | 0,000 | 0,029 |
| J79 | 0,352 | 0,025 | 0,000 | 0,003 | 0,000 | 0,002 | 0,000 | 0,002 | 0,000 | 0,010 |
| J90 | 0,021 | 0,272 | 0,001 | 0,085 | 0,001 | 0,073 | 0,001 | 0,046 | 0,000 | 0,231 |

|     | KO_1e11 / KO_1e12 | | KO_1e11 / WT | | KO_5e11 / KO_1e12 | | KO_5e11 / WT | | KO_1e12 / WT | |
|-----|-------|-------|-------|-------|-------|-------|-------|-------|-------|-------|
|     | MYOM3 | CK | MYOM3 | CK | MYOM3 | CK | MYOM3 | CK | MYOM3 | CK |
| J0  | 0,986 | 0,888 | 0,001 | 0,036 | 0,517 | 0,137 | 0,000 | 0,002 | 0,026 | 0,027 |
| J14 | 0,000 | 0,049 | 0,000 | 0,045 | 0,095 | 0,023 | 0,002 | 0,015 | 0,003 | 0,073 |
| J28 | 0,000 | 0,025 | 0,000 | 0,019 | 0,002 | 0,155 | 0,001 | 0,082 | 0,200 | 0,078 |
| J42 | 0,001 | 0,000 | 0,001 | 0,000 | 0,028 | 0,381 | 0,002 | 0,013 | 0,000 | 0,049 |
| J56 | 0,001 | 0,014 | 0,001 | 0,011 | 0,132 | 0,142 | 0,027 | 0,046 | 0,035 | 0,083 |
| J70 | 0,000 | 0,010 | 0,000 | 0,013 | 0,320 | 0,030 | 0,010 | 0,011 | 0,064 | 0,020 |
| J79 | 0,000 | 0,011 | 0,000 | 0,007 | 0,882 | 0,875 | 0,036 | 0,080 | 0,059 | 0,197 |
| J90 | 0,000 | 0,076 | 0,000 | 0,027 | 0,164 | 0,507 | 0,054 | 0,119 | 0,003 | 0,071 |

Figure 18 (cont.)

SEQUENCE LISTING

```
<160> NUMBER OF SEQ ID NOS: 25

<210> SEQ ID NO 1
<211> LENGTH: 1437
<212> TYPE: PRT
<213> ORGANISM: homo sapiens

<400> SEQUENCE: 1

Met Thr Leu Pro His Ser Leu Gly Gly Ala Gly Asp Pro Arg Pro Pro
1               5                   10                  15

Gln Ala Met Glu Val His Arg Leu Glu His Arg Gln Glu Glu Glu Gln
            20                  25                  30

Lys Glu Glu Arg Gln His Ser Leu Arg Met Gly Ser Ser Val Arg Arg
        35                  40                  45

Arg Thr Phe Arg Ser Ser Glu Glu Glu His Glu Phe Ser Ala Ala Asp
    50                  55                  60

Tyr Ala Leu Ala Ala Leu Ala Leu Thr Ala Ser Ser Glu Leu Ser
65                  70                  75                  80

Trp Glu Ala Gln Leu Arg Arg Gln Thr Ser Ala Val Glu Leu Glu Glu
                85                  90                  95

Arg Gly Gln Lys Arg Val Gly Phe Gly Asn Asp Trp Glu Arg Thr Glu
            100                 105                 110

Ile Ala Phe Leu Gln Thr His Arg Leu Leu Arg Gln Arg Arg Asp Trp
        115                 120                 125

Lys Thr Leu Arg Arg Arg Thr Glu Glu Lys Val Gln Glu Ala Lys Glu
    130                 135                 140
```

```
Leu Arg Glu Leu Cys Tyr Gly Arg Gly Pro Trp Phe Trp Ile Pro Leu
145                 150                 155                 160

Arg Ser His Ala Val Trp Glu His Thr Thr Val Leu Leu Thr Cys Thr
            165                 170                 175

Val Gln Ala Ser Pro Pro Gln Val Thr Trp Tyr Lys Asn Asp Thr
        180                 185                 190

Arg Ile Asp Pro Arg Leu Phe Arg Ala Gly Lys Tyr Arg Ile Thr Asn
    195                 200                 205

Asn Tyr Gly Leu Leu Ser Leu Glu Ile Arg Arg Cys Ala Ile Glu Asp
        210                 215                 220

Ser Ala Thr Tyr Thr Val Arg Val Lys Asn Ala His Gly Gln Ala Ser
225                 230                 235                 240

Ser Phe Ala Lys Val Leu Val Arg Thr Tyr Leu Gly Lys Asp Ala Gly
            245                 250                 255

Phe Asp Ser Glu Ile Phe Lys Arg Ser Thr Phe Gly Pro Ser Val Glu
            260                 265                 270

Phe Thr Ser Val Leu Lys Pro Val Phe Ala Arg Glu Lys Glu Pro Phe
        275                 280                 285

Ser Leu Ser Cys Leu Phe Ser Glu Asp Val Leu Asp Ala Glu Ser Ile
        290                 295                 300

Gln Trp Phe Arg Asp Gly Ser Leu Leu Arg Ser Ser Arg Arg Lys
305                 310                 315                 320

Ile Leu Tyr Thr Asp Arg Gln Ala Ser Leu Lys Val Ser Cys Thr Tyr
                325                 330                 335

Lys Glu Asp Glu Gly Leu Tyr Met Val Arg Val Pro Ser Pro Phe Gly
            340                 345                 350

Pro Arg Glu Gln Ser Thr Tyr Val Leu Val Arg Asp Ala Glu Ala Glu
            355                 360                 365

Asn Pro Gly Ala Pro Gly Ser Pro Leu Asn Val Arg Cys Leu Asp Val
        370                 375                 380

Asn Arg Asp Cys Leu Ile Leu Thr Trp Ala Pro Pro Ser Asp Thr Arg
385                 390                 395                 400

Gly Asn Pro Ile Thr Ala Tyr Thr Ile Glu Arg Cys Gln Gly Glu Ser
                405                 410                 415

Gly Glu Trp Ile Ala Cys His Glu Ala Pro Gly Gly Thr Cys Arg Cys
                420                 425                 430

Pro Ile Gln Gly Leu Val Glu Gly Gln Ser Tyr Arg Phe Arg Val Arg
        435                 440                 445

Ala Ile Ser Arg Val Gly Ser Ser Val Pro Ser Lys Ala Ser Glu Leu
        450                 455                 460

Val Val Met Gly Asp His Asp Ala Ala Arg Arg Lys Thr Glu Ile Pro
465                 470                 475                 480

Phe Asp Leu Gly Asn Lys Ile Thr Ile Ser Thr Asp Ala Phe Glu Asp
                485                 490                 495

Thr Val Thr Ile Pro Ser Pro Thr Asn Val His Ala Ser Glu Ile
            500                 505                 510

Arg Glu Ala Tyr Val Val Leu Ala Trp Glu Glu Pro Ser Pro Arg Asp
        515                 520                 525

Arg Ala Pro Leu Thr Tyr Ser Leu Glu Lys Ser Val Ile Gly Ser Gly
        530                 535                 540

Thr Trp Glu Ala Ile Ser Ser Glu Ser Pro Val Arg Ser Pro Arg Phe
545                 550                 555                 560

Ala Val Leu Asp Leu Glu Lys Lys Lys Ser Tyr Val Phe Arg Val Arg
```

-continued

```
                565                 570                 575
Ala Met Asn Gln Tyr Gly Leu Ser Asp Pro Ser Glu Pro Ser Glu Pro
                580                 585                 590

Ile Ala Leu Arg Gly Pro Pro Ala Thr Leu Pro Pro Pro Ala Gln Val
                595                 600                 605

Gln Ala Phe Arg Asp Thr Gln Thr Ser Val Ser Leu Thr Trp Asp Pro
            610                 615                 620

Val Lys Asp Pro Glu Leu Leu Gly Tyr Tyr Ile Tyr Ser Arg Lys Val
625                 630                 635                 640

Gly Thr Ser Glu Trp Gln Thr Val Asn Asn Lys Pro Ile Gln Gly Thr
                645                 650                 655

Arg Phe Thr Val Pro Gly Leu Arg Thr Gly Lys Glu Tyr Glu Phe Cys
                660                 665                 670

Val Arg Ser Val Ser Glu Ala Gly Val Gly Glu Ser Ser Ala Ala Thr
                675                 680                 685

Glu Pro Ile Arg Val Lys Gln Ala Leu Ala Thr Pro Ser Ala Pro Tyr
            690                 695                 700

Gly Phe Ala Leu Leu Asn Cys Gly Lys Asn Glu Met Val Ile Gly Trp
705                 710                 715                 720

Lys Pro Pro Lys Arg Gly Gly Gly Lys Ile Leu Gly Tyr Phe Leu
                725                 730                 735

Asp Gln His Asp Ser Glu Glu Leu Asp Trp His Ala Val Asn Gln Gln
            740                 745                 750

Pro Ile Pro Thr Arg Val Cys Lys Val Ser Asp Leu His Glu Gly His
            755                 760                 765

Phe Tyr Glu Phe Arg Ala Arg Ala Ala Asn Trp Ala Gly Val Gly Glu
            770                 775                 780

Leu Ser Ala Pro Ser Ser Leu Phe Glu Cys Lys Glu Trp Thr Met Pro
785                 790                 795                 800

Gln Pro Gly Pro Pro Tyr Asp Val Arg Ala Ser Glu Val Arg Ala Thr
                805                 810                 815

Ser Leu Val Leu Gln Trp Glu Pro Pro Leu Tyr Met Gly Ala Gly Pro
                820                 825                 830

Val Thr Gly Tyr His Val Ser Phe Gln Glu Glu Gly Ser Glu Gln Trp
                835                 840                 845

Lys Pro Val Thr Pro Gly Pro Ile Ser Gly Thr His Leu Arg Val Ser
850                 855                 860

Asp Leu Gln Pro Gly Lys Ser Tyr Val Phe Gln Val Gln Ala Met Asn
865                 870                 875                 880

Ser Ala Gly Leu Gly Gln Pro Ser Met Pro Thr Asp Pro Val Leu Leu
                885                 890                 895

Glu Asp Lys Pro Gly Ala His Glu Ile Glu Val Gly Val Asp Glu Glu
                900                 905                 910

Gly Phe Ile Tyr Leu Ala Phe Glu Ala Pro Glu Ala Pro Asp Ser Ser
            915                 920                 925

Glu Phe Gln Trp Ser Lys Asp Tyr Lys Gly Pro Leu Asp Pro Gln Arg
            930                 935                 940

Val Lys Ile Glu Asp Lys Val Asn Lys Ser Lys Val Ile Leu Lys Glu
945                 950                 955                 960

Pro Gly Leu Glu Asp Leu Gly Thr Tyr Ser Val Ile Val Thr Asp Ala
                965                 970                 975

Asp Glu Asp Ile Ser Ala Ser His Thr Leu Thr Glu Glu Glu Leu Glu
                980                 985                 990
```

```
Lys Leu Lys Lys Leu Ser His Glu  Ile Arg Asn Pro Val  Ile Lys Leu
        995              1000              1005

Ile Ser  Gly Trp Asn Ile Asp  Ile Leu Glu Arg Gly  Glu Val Arg
    1010              1015              1020

Leu Trp  Leu Glu Val Glu Lys  Leu Ser Pro Ala Ala  Glu Leu His
    1025              1030              1035

Leu Ile  Phe Asn Asn Lys Glu  Ile Phe Ser Ser Pro  Asn Arg Lys
    1040              1045              1050

Ile Asn  Phe Asp Arg Glu Lys  Gly Leu Val Glu Val  Ile Ile Gln
    1055              1060              1065

Asn Leu  Ser Glu Glu Asp Lys  Gly Ser Tyr Thr Ala  Gln Leu Gln
    1070              1075              1080

Asp Gly  Lys Ala Lys Asn Gln  Ile Thr Leu Thr Leu  Val Asp Asp
    1085              1090              1095

Asp Phe  Asp Lys Leu Leu Arg  Lys Ala Asp Ala Lys  Arg Arg Asp
    1100              1105              1110

Trp Lys  Arg Lys Gln Gly Pro  Tyr Phe Glu Arg Pro  Leu Gln Trp
    1115              1120              1125

Lys Val  Thr Glu Asp Cys Gln  Val Gln Leu Thr Cys  Lys Val Thr
    1130              1135              1140

Asn Thr  Lys Lys Glu Thr Arg  Phe Gln Trp Phe Phe  Gln Arg Ala
    1145              1150              1155

Glu Met  Pro Asp Gly Gln Tyr  Asp Pro Glu Thr Gly  Thr Gly Leu
    1160              1165              1170

Leu Cys  Ile Glu Glu Leu Ser  Lys Lys Asp Lys Gly  Ile Tyr Arg
    1175              1180              1185

Ala Met  Val Ser Asp Asp Arg  Gly Glu Asp Asp Thr  Ile Leu Asp
    1190              1195              1200

Leu Thr  Gly Asp Ala Leu Asp  Ala Ile Phe Thr Glu  Leu Gly Arg
    1205              1210              1215

Ile Gly  Ala Leu Ser Ala Thr  Pro Leu Lys Ile Gln  Gly Thr Glu
    1220              1225              1230

Glu Gly  Ile Arg Ile Phe Ser  Lys Val Lys Tyr Tyr  Asn Val Glu
    1235              1240              1245

Tyr Met  Lys Thr Thr Trp Phe  His Lys Asp Lys Arg  Leu Glu Ser
    1250              1255              1260

Gly Asp  Arg Ile Arg Thr Gly  Thr Thr Leu Asp Glu  Ile Trp Leu
    1265              1270              1275

His Ile  Leu Asp Pro Lys Asp  Ser Asp Lys Gly Lys  Tyr Thr Leu
    1280              1285              1290

Glu Ile  Ala Ala Gly Lys Glu  Val Arg Gln Leu Ser  Thr Asp Leu
    1295              1300              1305

Ser Gly  Gln Ala Phe Glu Asp  Ala Met Ala Glu His  Gln Arg Leu
    1310              1315              1320

Lys Thr  Leu Ala Ile Ile Glu  Lys Asn Arg Ala Lys  Val Val Arg
    1325              1330              1335

Gly Leu  Pro Asp Val Ala Thr  Ile Met Glu Asp Lys  Thr Leu Cys
    1340              1345              1350

Leu Thr  Cys Ile Val Ser Gly  Asp Pro Thr Pro Glu  Ile Ser Trp
    1355              1360              1365

Leu Lys  Asn Asp Gln Pro Val  Thr Phe Leu Asp Arg  Tyr Arg Met
    1370              1375              1380
```

```
Glu Val Arg Gly Thr Glu Val Thr Ile Thr Ile Glu Lys Val Asn
    1385                1390                1395

Ser Glu Asp Ser Gly Arg Tyr Gly Val Phe Val Lys Asn Lys Tyr
    1400                1405                1410

Gly Ser Glu Thr Gly Gln Val Thr Ile Ser Val Phe Lys His Gly
    1415                1420                1425

Asp Glu Pro Lys Glu Leu Lys Ser Met
    1430                1435

<210> SEQ ID NO 2
<211> LENGTH: 9
<212> TYPE: PRT
<213> ORGANISM: homo sapiens

<400> SEQUENCE: 2

Glu Gln Ser Thr Tyr Val Leu Val Arg
1               5

<210> SEQ ID NO 3
<211> LENGTH: 17
<212> TYPE: PRT
<213> ORGANISM: homo sapiens

<400> SEQUENCE: 3

Asp Ala Glu Ala Glu Asn Pro Gly Ala Pro Gly Ser Pro Leu Asn Val
1               5                   10                  15
Arg

<210> SEQ ID NO 4
<211> LENGTH: 14
<212> TYPE: PRT
<213> ORGANISM: homo sapiens

<400> SEQUENCE: 4

Ala Ser Glu Leu Val Val Met Gly Asp His Asp Ala Ala Arg
1               5                   10

<210> SEQ ID NO 5
<211> LENGTH: 18
<212> TYPE: PRT
<213> ORGANISM: homo sapiens

<400> SEQUENCE: 5

Ser Val Ile Gly Ser Gly Thr Trp Glu Ala Ile Ser Ser Glu Ser Pro
1               5                   10                  15
Val Arg

<210> SEQ ID NO 6
<211> LENGTH: 8
<212> TYPE: PRT
<213> ORGANISM: homo sapiens

<400> SEQUENCE: 6

Phe Ala Val Leu Asp Leu Glu Lys
1               5

<210> SEQ ID NO 7
<211> LENGTH: 20
<212> TYPE: PRT
<213> ORGANISM: homo sapiens

<400> SEQUENCE: 7
```

Ala Met Asn Gln Tyr Gly Leu Ser Asp Pro Ser Glu Pro Ser Glu Pro
1               5                   10                  15

Ile Ala Leu Arg
            20

<210> SEQ ID NO 8
<211> LENGTH: 18
<212> TYPE: PRT
<213> ORGANISM: homo sapiens

<400> SEQUENCE: 8

Val Gly Thr Ser Glu Trp Gln Thr Val Asn Asn Lys Pro Ile Gln Gly
1               5                   10                  15

Thr Arg

<210> SEQ ID NO 9
<211> LENGTH: 19
<212> TYPE: PRT
<213> ORGANISM: homo sapiens

<400> SEQUENCE: 9

Gln Ala Leu Ala Thr Pro Ser Ala Pro Tyr Gly Phe Ala Leu Leu Asn
1               5                   10                  15

Cys Gly Lys

<210> SEQ ID NO 10
<211> LENGTH: 13
<212> TYPE: PRT
<213> ORGANISM: homo sapiens

<400> SEQUENCE: 10

Val Ser Asp Leu His Glu Gly His Phe Tyr Glu Phe Arg
1               5                   10

<210> SEQ ID NO 11
<211> LENGTH: 20
<212> TYPE: PRT
<213> ORGANISM: homo sapiens

<400> SEQUENCE: 11

Ala Ala Asn Trp Ala Gly Val Gly Glu Leu Ser Ala Pro Ser Ser Leu
1               5                   10                  15

Phe Glu Cys Lys
            20

<210> SEQ ID NO 12
<211> LENGTH: 12
<212> TYPE: PRT
<213> ORGANISM: homo sapiens

<400> SEQUENCE: 12

Leu Ile Ser Gly Trp Asn Ile Asp Ile Leu Glu Arg
1               5                   10

<210> SEQ ID NO 13
<211> LENGTH: 11
<212> TYPE: PRT
<213> ORGANISM: homo sapiens

<400> SEQUENCE: 13

Gly Ser Tyr Thr Ala Gln Leu Gln Asp Gly Lys
1               5                   10

```
<210> SEQ ID NO 14
<211> LENGTH: 12
<212> TYPE: PRT
<213> ORGANISM: homo sapiens

<400> SEQUENCE: 14

Val Thr Glu Asp Cys Gln Val Gln Leu Thr Cys Lys
1               5                   10

<210> SEQ ID NO 15
<211> LENGTH: 10
<212> TYPE: PRT
<213> ORGANISM: homo sapiens

<400> SEQUENCE: 15

Ile Gly Ala Leu Ser Ala Thr Pro Leu Lys
1               5                   10

<210> SEQ ID NO 16
<211> LENGTH: 20
<212> TYPE: PRT
<213> ORGANISM: homo sapiens

<400> SEQUENCE: 16

Gln Leu Ser Thr Asp Leu Ser Gly Gln Ala Phe Glu Asp Ala Met Ala
1               5                   10                  15

Glu His Gln Arg
            20

<210> SEQ ID NO 17
<211> LENGTH: 24
<212> TYPE: DNA
<213> ORGANISM: artificial
<220> FEATURE:
<223> OTHER INFORMATION: primer

<400> SEQUENCE: 17
ctccatcact aggggttcct tgta                                              24

<210> SEQ ID NO 18
<211> LENGTH: 25
<212> TYPE: DNA
<213> ORGANISM: artificial
<220> FEATURE:
<223> OTHER INFORMATION: primer

<400> SEQUENCE: 18
tggctacgta gataagtagc atggc                                             25

<210> SEQ ID NO 19
<211> LENGTH: 15
<212> TYPE: DNA
<213> ORGANISM: artificial
<220> FEATURE:
<223> OTHER INFORMATION: probe

<400> SEQUENCE: 19
gttaatgatt aaccc                                                        15

<210> SEQ ID NO 20
<211> LENGTH: 22
<212> TYPE: DNA
<213> ORGANISM: artificial
<220> FEATURE:
<223> OTHER INFORMATION: primer
```

<400> SEQUENCE: 20
gctgtcatct cttgtgggct gt                                           22

<210> SEQ ID NO 21
<211> LENGTH: 21
<212> TYPE: DNA
<213> ORGANISM: artificial
<220> FEATURE:
<223> OTHER INFORMATION: primer

<400> SEQUENCE: 21
actcatggga gctgctggtt c                                            21

<210> SEQ ID NO 22
<211> LENGTH: 26
<212> TYPE: DNA
<213> ORGANISM: artificial
<220> FEATURE:
<223> OTHER INFORMATION: probe

<400> SEQUENCE: 22
cctgtcatgc ccacacaaat ctctcc                                       26

<210> SEQ ID NO 23
<211> LENGTH: 1685
<212> TYPE: PRT
<213> ORGANISM: homo sapiens

<400> SEQUENCE: 23

```
Met Ser Leu Pro Phe Tyr Gln Arg Cys His Gln His Tyr Asp Leu Ser
1               5                   10                  15

Tyr Arg Asn Lys Asp Val Arg Ser Thr Val Ser His Tyr Gln Arg Glu
            20                  25                  30

Lys Lys Arg Ser Ala Val Tyr Thr Gln Gly Ser Thr Ala Tyr Ser Ser
        35                  40                  45

Arg Ser Ser Ala Ala His Arg Glu Ser Glu Ala Phe Arg Arg Ala
    50                  55                  60

Ser Ala Ser Ser Ser Gln Gln Ala Ser Gln His Ala Leu Ser Ser
65                  70                  75                  80

Glu Val Ser Arg Lys Ala Ala Ser Ala Tyr Asp Tyr Gly Ser Ser His
                85                  90                  95

Gly Leu Thr Asp Ser Ser Leu Leu Asp Asp Tyr Ser Ser Lys Leu
            100                 105                 110

Ser Pro Lys Pro Lys Arg Ala Lys His Ser Leu Leu Ser Gly Glu Glu
        115                 120                 125

Lys Glu Asn Leu Pro Ser Asp Tyr Met Val Pro Ile Phe Ser Gly Arg
    130                 135                 140

Gln Lys His Val Ser Gly Ile Thr Asp Thr Glu Glu Arg Ile Lys
145                 150                 155                 160

Glu Ala Ala Ala Tyr Ile Ala Gln Arg Asn Leu Leu Ala Ser Glu Glu
                165                 170                 175

Gly Ile Thr Thr Ser Lys Gln Ser Thr Ala Ser Lys Gln Thr Thr Ala
            180                 185                 190

Ser Lys Gln Ser Thr Ala Ser Lys Gln Ser Thr Ala Ser Lys Gln Ser
        195                 200                 205

Thr Ala Ser Arg Gln Ser Thr Ala Ser Arg Gln Ser Val Val Ser Lys
    210                 215                 220
```

```
Gln Ala Thr Ser Ala Leu Gln Gln Glu Glu Thr Ser Glu Lys Lys Ser
225                 230                 235                 240

Arg Lys Val Val Ile Arg Glu Lys Ala Glu Arg Leu Ser Leu Arg Lys
            245                 250                 255

Thr Leu Glu Glu Thr Glu Thr Tyr His Ala Lys Leu Asn Glu Asp His
        260                 265                 270

Leu Leu His Ala Pro Glu Phe Ile Ile Lys Pro Arg Ser His Thr Val
    275                 280                 285

Trp Glu Lys Glu Asn Val Lys Leu His Cys Ser Ile Ala Gly Trp Pro
290                 295                 300

Glu Pro Arg Val Thr Trp Tyr Lys Asn Gln Val Pro Ile Asn Val His
305                 310                 315                 320

Ala Asn Pro Gly Lys Tyr Ile Ile Glu Ser Arg Tyr Gly Met His Thr
                325                 330                 335

Leu Glu Ile Asn Gly Cys Asp Phe Glu Asp Thr Ala Gln Tyr Arg Ala
            340                 345                 350

Ser Ala Met Asn Val Lys Gly Glu Leu Ser Ala Tyr Ala Ser Val Val
        355                 360                 365

Val Lys Arg Tyr Lys Gly Glu Phe Asp Glu Thr Arg Phe His Ala Gly
370                 375                 380

Ala Ser Thr Met Pro Leu Ser Phe Gly Val Thr Pro Tyr Gly Tyr Ala
385                 390                 395                 400

Ser Arg Phe Glu Ile His Phe Asp Asp Lys Phe Asp Val Ser Phe Gly
                405                 410                 415

Arg Glu Gly Glu Thr Met Ser Leu Gly Cys Arg Val Val Ile Thr Pro
            420                 425                 430

Glu Ile Lys His Phe Gln Pro Glu Ile Gln Trp Tyr Arg Asn Gly Val
        435                 440                 445

Pro Leu Ser Pro Ser Lys Trp Val Gln Thr Leu Trp Ser Gly Glu Arg
    450                 455                 460

Ala Thr Leu Thr Phe Ser His Leu Asn Lys Glu Asp Glu Gly Leu Tyr
465                 470                 475                 480

Thr Ile Arg Val Arg Met Gly Glu Tyr Tyr Glu Gln Tyr Ser Ala Tyr
                485                 490                 495

Val Phe Val Arg Asp Ala Asp Ala Glu Ile Glu Gly Ala Pro Ala Ala
            500                 505                 510

Pro Leu Asp Val Lys Cys Leu Glu Ala Asn Lys Asp Tyr Ile Ile Ile
        515                 520                 525

Ser Trp Lys Gln Pro Ala Val Asp Gly Gly Ser Pro Ile Leu Gly Tyr
    530                 535                 540

Phe Ile Asp Lys Cys Glu Val Gly Thr Asp Ser Trp Ser Gln Cys Asn
545                 550                 555                 560

Asp Thr Pro Val Lys Phe Ala Arg Phe Pro Val Thr Gly Leu Ile Glu
                565                 570                 575

Gly Arg Ser Tyr Ile Phe Arg Val Arg Ala Val Asn Lys Met Gly Ile
            580                 585                 590

Gly Phe Pro Ser Arg Val Ser Glu Pro Val Ala Ala Leu Asp Pro Ala
        595                 600                 605

Glu Lys Ala Arg Leu Lys Ser Arg Pro Ser Ala Pro Trp Thr Gly Gln
    610                 615                 620

Ile Ile Val Thr Glu Glu Pro Ser Glu Gly Ile Val Pro Gly Pro
625                 630                 635                 640

Pro Thr Asp Leu Ser Val Thr Glu Ala Thr Arg Ser Tyr Val Val Leu
```

-continued

```
                645                 650                 655
Ser Trp Lys Pro Pro Gly Gln Arg Gly His Glu Gly Ile Met Tyr Phe
            660                 665                 670

Val Glu Lys Cys Glu Ala Gly Thr Glu Asn Trp Gln Arg Val Asn Thr
            675                 680                 685

Glu Leu Pro Val Lys Ser Pro Arg Phe Ala Leu Phe Asp Leu Ala Glu
        690                 695                 700

Gly Lys Ser Tyr Cys Phe Arg Val Arg Cys Ser Asn Ser Ala Gly Val
705                 710                 715                 720

Gly Glu Pro Ser Glu Ala Thr Glu Val Thr Val Gly Asp Lys Leu
                725                 730                 735

Asp Ile Pro Lys Ala Pro Gly Lys Ile Ile Pro Ser Arg Asn Thr Asp
            740                 745                 750

Thr Ser Val Val Val Ser Trp Glu Glu Ser Lys Asp Ala Lys Glu Leu
                755                 760                 765

Val Gly Tyr Tyr Ile Glu Ala Ser Val Ala Gly Ser Gly Lys Trp Glu
            770                 775                 780

Pro Cys Asn Asn Asn Pro Val Lys Gly Ser Arg Phe Thr Cys His Gly
785                 790                 795                 800

Leu Val Thr Gly Gln Ser Tyr Ile Phe Arg Val Arg Ala Val Asn Ala
                805                 810                 815

Ala Gly Leu Ser Glu Tyr Ser Gln Asp Ser Glu Ala Ile Glu Val Lys
            820                 825                 830

Ala Ala Ile Gly Gly Gly Val Ser Pro Asp Val Cys Pro Ala Leu Ser
            835                 840                 845

Asp Glu Pro Gly Gly Leu Thr Ala Ser Arg Gly Arg Val His Glu Ala
        850                 855                 860

Ser Pro Pro Thr Phe Gln Lys Asp Ala Leu Leu Gly Ser Lys Pro Asn
865                 870                 875                 880

Lys Pro Ser Leu Pro Ser Ser Ser Gln Asn Leu Gly Gln Thr Glu Val
                885                 890                 895

Ser Lys Val Ser Glu Thr Val Gln Glu Glu Leu Thr Pro Pro Pro Gln
            900                 905                 910

Lys Ala Ala Pro Gln Gly Lys Ser Lys Ser Asp Pro Leu Lys Lys Lys
        915                 920                 925

Thr Asp Arg Ala Pro Pro Ser Pro Pro Cys Asp Ile Thr Cys Leu Glu
        930                 935                 940

Ser Phe Arg Asp Ser Met Val Leu Gly Trp Lys Gln Pro Asp Lys Ile
945                 950                 955                 960

Gly Gly Ala Glu Ile Thr Gly Tyr Tyr Val Asn Tyr Arg Glu Val Ile
                965                 970                 975

Asp Gly Val Pro Gly Lys Trp Arg Glu Ala Asn Val Lys Ala Val Ser
            980                 985                 990

Glu Glu Ala Tyr Lys Ile Ser Asn Leu Lys Glu Asn Met Val Tyr Gln
        995                 1000                1005

Phe Gln Val Ala Ala Met Asn Met Ala Gly Leu Gly Ala Pro Ser
    1010                1015                1020

Ala Val Ser Glu Cys Phe Lys Cys Glu Glu Trp Thr Ile Ala Val
    1025                1030                1035

Pro Gly Pro Pro His Ser Leu Lys Cys Ser Glu Val Arg Lys Asp
    1040                1045                1050

Ser Leu Val Leu Gln Trp Lys Pro Pro Val His Ser Gly Arg Thr
    1055                1060                1065
```

```
Pro Val Thr Gly Tyr Phe Val Asp Leu Lys Glu Ala Lys Ala Lys
    1070                1075                1080

Glu Asp Gln Trp Arg Gly Leu Asn Glu Ala Ala Ile Lys Asn Val
    1085                1090                1095

Tyr Leu Lys Val Arg Gly Leu Lys Glu Gly Val Ser Tyr Val Phe
    1100                1105                1110

Arg Val Arg Ala Ile Asn Gln Ala Gly Val Gly Lys Pro Ser Asp
    1115                1120                1125

Leu Ala Gly Pro Val Val Ala Glu Thr Arg Pro Gly Thr Lys Glu
    1130                1135                1140

Val Val Val Asn Val Asp Asp Gly Val Ile Ser Leu Asn Phe
    1145                1150                1155

Glu Cys Asp Lys Met Thr Pro Lys Ser Glu Phe Ser Trp Ser Lys
    1160                1165                1170

Asp Tyr Val Ser Thr Glu Asp Ser Pro Arg Leu Glu Val Glu Ser
    1175                1180                1185

Lys Gly Asn Lys Thr Lys Met Thr Phe Lys Asp Leu Gly Met Asp
    1190                1195                1200

Asp Leu Gly Ile Tyr Ser Cys Asp Val Thr Asp Thr Asp Gly Ile
    1205                1210                1215

Ala Ser Ser Tyr Leu Ile Asp Glu Glu Glu Leu Lys Arg Leu Leu
    1220                1225                1230

Ala Leu Ser His Glu His Lys Phe Pro Thr Val Pro Val Lys Ser
    1235                1240                1245

Glu Leu Ala Val Glu Ile Leu Glu Lys Gly Gln Val Arg Phe Trp
    1250                1255                1260

Met Gln Ala Glu Lys Leu Ser Gly Asn Ala Lys Val Asn Tyr Ile
    1265                1270                1275

Phe Asn Glu Lys Glu Ile Phe Glu Gly Pro Lys Tyr Lys Met His
    1280                1285                1290

Ile Asp Arg Asn Thr Gly Ile Ile Glu Met Phe Met Glu Lys Leu
    1295                1300                1305

Gln Asp Glu Asp Glu Gly Thr Tyr Thr Phe Gln Leu Gln Asp Gly
    1310                1315                1320

Lys Ala Thr Asn His Ser Thr Val Val Leu Val Gly Asp Val Phe
    1325                1330                1335

Lys Lys Leu Gln Lys Glu Ala Glu Phe Gln Arg Gln Glu Trp Ile
    1340                1345                1350

Arg Lys Gln Gly Pro His Phe Val Glu Tyr Leu Ser Trp Glu Val
    1355                1360                1365

Thr Gly Glu Cys Asn Val Leu Leu Lys Cys Lys Val Ala Asn Ile
    1370                1375                1380

Lys Lys Glu Thr His Ile Val Trp Tyr Lys Asp Glu Arg Glu Ile
    1385                1390                1395

Ser Val Asp Glu Lys His Asp Phe Lys Asp Gly Ile Cys Thr Leu
    1400                1405                1410

Leu Ile Thr Glu Phe Ser Lys Lys Asp Ala Gly Ile Tyr Glu Val
    1415                1420                1425

Ile Leu Lys Asp Asp Arg Gly Lys Asp Lys Ser Arg Leu Lys Leu
    1430                1435                1440

Val Asp Glu Ala Phe Lys Glu Leu Met Met Glu Val Cys Lys Lys
    1445                1450                1455
```

```
Ile Ala Leu Ser Ala Thr Asp Leu Lys Ile Gln Ser Thr Ala Glu
    1460                1465                1470

Gly Ile Gln Leu Tyr Ser Phe Val Thr Tyr Tyr Val Glu Asp Leu
    1475                1480                1485

Lys Val Asn Trp Ser His Asn Gly Ser Ala Ile Arg Tyr Ser Asp
    1490                1495                1500

Arg Val Lys Thr Gly Val Thr Gly Glu Gln Ile Trp Leu Gln Ile
    1505                1510                1515

Asn Glu Pro Thr Pro Asn Asp Lys Gly Lys Tyr Val Met Glu Leu
    1520                1525                1530

Phe Asp Gly Lys Thr Gly His Gln Lys Thr Val Asp Leu Ser Gly
    1535                1540                1545

Gln Ala Tyr Asp Glu Ala Tyr Ala Glu Phe Gln Arg Leu Lys Gln
    1550                1555                1560

Ala Ala Ile Ala Glu Lys Asn Arg Ala Arg Val Leu Gly Gly Leu
    1565                1570                1575

Pro Asp Val Val Thr Ile Gln Glu Gly Lys Ala Leu Asn Leu Thr
    1580                1585                1590

Cys Asn Val Trp Gly Asp Pro Pro Pro Glu Val Ser Trp Leu Lys
    1595                1600                1605

Asn Glu Lys Ala Leu Ala Ser Asp Asp His Cys Asn Leu Lys Phe
    1610                1615                1620

Glu Ala Gly Arg Thr Ala Tyr Phe Thr Ile Asn Gly Val Ser Thr
    1625                1630                1635

Ala Asp Ser Gly Lys Tyr Gly Leu Val Val Lys Asn Lys Tyr Gly
    1640                1645                1650

Ser Glu Thr Ser Asp Phe Thr Val Ser Val Phe Ile Pro Glu Glu
    1655                1660                1665

Glu Ala Arg Met Ala Ala Leu Glu Ser Leu Lys Gly Gly Lys Lys
    1670                1675                1680

Ala Lys
    1685

<210> SEQ ID NO 24
<211> LENGTH: 1465
<212> TYPE: PRT
<213> ORGANISM: homo sapiens

<400> SEQUENCE: 24

Met Ser Leu Val Thr Val Pro Phe Tyr Gln Lys Arg His Arg His Phe
1               5                   10                  15

Asp Gln Ser Tyr Arg Asn Ile Gln Thr Arg Tyr Leu Leu Asp Glu Tyr
            20                  25                  30

Ala Ser Lys Lys Arg Ala Ser Thr Gln Ala Ser Ser Gln Lys Ser Leu
        35                  40                  45

Ser Gln Arg Ser Ser Ser Gln Arg Ala Ser Ser Gln Thr Ser Leu Gly
    50                  55                  60

Gly Thr Ile Cys Arg Val Cys Ala Lys Arg Val Ser Thr Gln Glu Asp
65                  70                  75                  80

Glu Glu Gln Glu Asn Arg Ser Arg Tyr Gln Ser Leu Val Ala Ala Tyr
                85                  90                  95

Gly Glu Ala Lys Arg Gln Arg Phe Leu Ser Glu Leu Ala His Leu Glu
            100                 105                 110

Glu Asp Val His Leu Ala Arg Ser Gln Ala Arg Asp Lys Leu Asp Lys
        115                 120                 125
```

```
Tyr Ala Ile Gln Gln Met Met Glu Asp Lys Leu Ala Trp Glu Arg His
    130                 135                 140

Thr Phe Glu Glu Arg Ile Ser Arg Ala Pro Glu Ile Leu Val Arg Leu
145                 150                 155                 160

Arg Ser His Thr Val Trp Glu Arg Met Ser Val Lys Leu Cys Phe Thr
                165                 170                 175

Val Gln Gly Phe Pro Thr Pro Val Val Gln Trp Tyr Lys Asp Gly Ser
            180                 185                 190

Leu Ile Cys Gln Ala Ala Glu Pro Gly Lys Tyr Arg Ile Glu Ser Asn
        195                 200                 205

Tyr Gly Val His Thr Leu Glu Ile Asn Arg Ala Asp Phe Asp Asp Thr
    210                 215                 220

Ala Thr Tyr Ser Ala Val Ala Thr Asn Ala His Gly Gln Val Ser Thr
225                 230                 235                 240

Asn Ala Ala Val Val Val Arg Arg Phe Arg Gly Asp Glu Glu Pro Phe
                245                 250                 255

Arg Ser Val Gly Leu Pro Ile Gly Leu Pro Leu Ser Ser Met Ile Pro
                260                 265                 270

Tyr Thr His Phe Asp Val Gln Phe Leu Glu Lys Phe Gly Val Thr Phe
            275                 280                 285

Arg Arg Glu Gly Glu Thr Val Thr Leu Lys Cys Thr Met Leu Val Thr
        290                 295                 300

Pro Asp Leu Lys Arg Val Gln Pro Arg Ala Glu Trp Tyr Arg Asp Asp
305                 310                 315                 320

Val Leu Leu Lys Glu Ser Lys Trp Thr Lys Met Phe Phe Gly Glu Gly
                325                 330                 335

Gln Ala Ser Leu Ser Phe Ser His Leu His Lys Asp Asp Glu Gly Leu
                340                 345                 350

Tyr Thr Leu Arg Ile Val Ser Arg Gly Gly Val Ser Asp His Ser Ala
            355                 360                 365

Phe Leu Phe Val Arg Asp Ala Asp Pro Leu Val Thr Gly Ala Pro Gly
    370                 375                 380

Ala Pro Met Asp Leu Gln Cys His Asp Ala Asn Arg Asp Tyr Val Ile
385                 390                 395                 400

Val Thr Trp Lys Pro Pro Asn Thr Thr Glu Ser Pro Val Met Gly
                405                 410                 415

Tyr Phe Val Asp Arg Cys Glu Val Gly Thr Asn Asn Trp Val Gln Cys
            420                 425                 430

Asn Asp Ala Pro Val Lys Ile Cys Lys Tyr Pro Val Thr Gly Leu Phe
        435                 440                 445

Glu Gly Arg Ser Tyr Ile Phe Arg Val Arg Ala Val Asn Ser Ala Gly
    450                 455                 460

Ile Ser Arg Pro Ser Arg Val Ser Asp Ala Val Ala Ala Leu Asp Pro
465                 470                 475                 480

Leu Asp Leu Arg Arg Leu Gln Ala Val His Leu Glu Gly Glu Lys Glu
                485                 490                 495

Ile Ala Ile Tyr Gln Asp Asp Leu Glu Gly Asp Ala Gln Val Pro Gly
            500                 505                 510

Pro Pro Thr Gly Val His Ala Ser Glu Ile Ser Arg Asn Tyr Val Val
        515                 520                 525

Leu Ser Trp Glu Pro Pro Thr Pro Arg Gly Lys Asp Pro Leu Met Tyr
    530                 535                 540
```

```
Phe Ile Glu Lys Ser Val Gly Ser Gly Ser Trp Gln Arg Val Asn
545                 550                 555                 560

Ala Gln Thr Ala Val Arg Ser Pro Arg Tyr Ala Val Phe Asp Leu Met
                565                 570                 575

Glu Gly Lys Ser Tyr Val Phe Arg Val Leu Ser Ala Asn Arg His Gly
                580                 585                 590

Leu Ser Glu Pro Ser Glu Ile Thr Ser Pro Ile Gln Ala Gln Asp Val
                595                 600                 605

Thr Val Val Pro Ser Ala Pro Gly Arg Val Leu Ala Ser Arg Asn Thr
610                 615                 620

Lys Thr Ser Val Val Gln Trp Asp Arg Pro Lys His Glu Glu Asp
625                 630                 635                 640

Leu Leu Gly Tyr Tyr Val Asp Cys Cys Val Ala Gly Thr Asn Leu Trp
                645                 650                 655

Glu Pro Cys Asn His Lys Pro Ile Gly Tyr Asn Arg Phe Val Val His
                660                 665                 670

Gly Leu Thr Thr Gly Glu Gln Tyr Ile Phe Arg Val Lys Ala Val Asn
                675                 680                 685

Ala Val Gly Met Ser Glu Asn Ser Gln Glu Ser Asp Val Ile Lys Val
                690                 695                 700

Gln Ala Ala Leu Thr Val Pro Ser His Pro Tyr Gly Ile Thr Leu Leu
705                 710                 715                 720

Asn Cys Asp Gly His Ser Met Thr Leu Gly Trp Lys Val Pro Lys Phe
                725                 730                 735

Ser Gly Gly Ser Pro Ile Leu Gly Tyr Tyr Leu Asp Lys Arg Glu Val
                740                 745                 750

His His Lys Asn Trp His Glu Val Asn Ser Ser Pro Ser Lys Pro Thr
                755                 760                 765

Ile Leu Thr Val Asp Gly Leu Thr Glu Gly Ser Leu Tyr Glu Phe Lys
770                 775                 780

Ile Ala Ala Val Asn Leu Ala Gly Ile Gly Glu Pro Ser Asp Pro Ser
785                 790                 795                 800

Glu His Phe Lys Cys Glu Ala Trp Thr Met Pro Glu Pro Gly Pro Ala
                805                 810                 815

Tyr Asp Leu Thr Phe Cys Glu Val Arg Asp Thr Ser Leu Val Met Leu
                820                 825                 830

Trp Lys Ala Pro Val Tyr Ser Gly Ser Ser Pro Val Ser Gly Tyr Phe
                835                 840                 845

Val Asp Phe Arg Glu Glu Asp Ala Gly Glu Trp Ile Thr Val Asn Gln
                850                 855                 860

Thr Thr Thr Ala Asn Arg Tyr Leu Lys Val Ser Asp Leu Gln Gln Gly
865                 870                 875                 880

Lys Thr Tyr Val Phe Arg Val Arg Ala Val Asn Ala Asn Gly Val Gly
                885                 890                 895

Lys Pro Ser Asp Thr Ser Glu Pro Val Leu Val Glu Ala Arg Pro Gly
                900                 905                 910

Thr Lys Glu Ile Ser Ala Gly Val Asp Glu Gln Gly Asn Ile Tyr Leu
                915                 920                 925

Gly Phe Asp Cys Gln Glu Met Thr Asp Ala Ser Gln Phe Thr Trp Cys
                930                 935                 940

Lys Ser Tyr Glu Glu Ile Ser Asp Asp Glu Arg Phe Lys Ile Glu Thr
945                 950                 955                 960

Val Gly Asp His Ser Lys Leu Tyr Leu Lys Asn Pro Asp Lys Glu Asp
```

-continued

```
                965                 970                 975
Leu Gly Thr Tyr Ser Val Ser Val Ser Asp Thr Asp Gly Val Ser Ser
                    980                 985                 990
Ser Phe Val Leu Asp Pro Glu Glu Leu Glu Arg Leu Met Ala Leu Ser
           995                1000                1005
Asn Glu Ile Lys Asn Pro Thr Ile Pro Leu Lys Ser Glu Leu Ala
       1010                1015                1020
Tyr Glu Ile Phe Asp Lys Gly Arg Val Arg Phe Trp Leu Gln Ala
       1025                1030                1035
Glu His Leu Ser Pro Asp Ala Ser Tyr Arg Phe Ile Ile Asn Asp
       1040                1045                1050
Arg Glu Val Ser Asp Ser Glu Ile His Arg Ile Lys Cys Asp Lys
       1055                1060                1065
Ala Thr Gly Ile Ile Glu Met Val Met Asp Arg Phe Ser Ile Glu
       1070                1075                1080
Asn Glu Gly Thr Tyr Thr Val Gln Ile His Asp Gly Lys Ala Lys
       1085                1090                1095
Ser Gln Ser Ser Leu Val Leu Ile Gly Asp Ala Phe Lys Thr Val
       1100                1105                1110
Leu Glu Glu Ala Glu Phe Gln Arg Lys Glu Phe Leu Arg Lys Gln
       1115                1120                1125
Gly Pro His Phe Ala Glu Tyr Leu His Trp Asp Val Thr Glu Glu
       1130                1135                1140
Cys Glu Val Arg Leu Val Cys Lys Val Ala Asn Thr Lys Lys Glu
       1145                1150                1155
Thr Val Phe Lys Trp Leu Lys Asp Val Leu Tyr Glu Thr Glu
       1160                1165                1170
Thr Leu Pro Asn Leu Glu Arg Gly Ile Cys Glu Leu Leu Ile Pro
       1175                1180                1185
Lys Leu Ser Lys Lys Asp His Gly Glu Tyr Lys Ala Thr Leu Lys
       1190                1195                1200
Asp Asp Arg Gly Gln Asp Val Ser Ile Leu Glu Ile Ala Gly Lys
       1205                1210                1215
Val Tyr Asp Asp Met Ile Leu Ala Met Ser Arg Val Cys Gly Lys
       1220                1225                1230
Ser Ala Ser Pro Leu Lys Val Leu Cys Thr Pro Glu Gly Ile Arg
       1235                1240                1245
Leu Gln Cys Phe Met Lys Tyr Phe Thr Asp Glu Met Lys Val Asn
       1250                1255                1260
Trp Cys His Lys Asp Ala Lys Ile Ser Ser Ser Glu His Met Arg
       1265                1270                1275
Ile Gly Gly Ser Glu Glu Met Ala Trp Leu Gln Ile Cys Glu Pro
       1280                1285                1290
Thr Glu Lys Asp Lys Gly Lys Tyr Thr Phe Glu Ile Phe Asp Gly
       1295                1300                1305
Lys Asp Asn His Gln Arg Ser Leu Asp Leu Ser Gly Gln Ala Phe
       1310                1315                1320
Asp Glu Ala Phe Ala Glu Phe Gln Gln Phe Lys Ala Ala Ala Phe
       1325                1330                1335
Ala Glu Lys Asn Arg Gly Arg Leu Ile Gly Gly Leu Pro Asp Val
       1340                1345                1350
Val Thr Ile Met Glu Gly Lys Thr Leu Asn Leu Thr Cys Thr Val
       1355                1360                1365
```

```
Phe Gly Asn Pro Asp Pro Glu Val Ile Trp Phe Lys Asn Asp Gln
    1370                1375            1380

Asp Ile Gln Leu Ser Glu His Phe Ser Val Lys Val Glu Gln Ala
    1385                1390            1395

Lys Tyr Val Ser Met Thr Ile Lys Gly Val Thr Ser Glu Asp Ser
    1400                1405            1410

Gly Lys Tyr Ser Ile Asn Ile Lys Asn Lys Tyr Gly Gly Glu Lys
    1415                1420            1425

Ile Asp Val Thr Val Ser Val Tyr Lys His Gly Glu Lys Ile Pro
    1430                1435            1440

Asp Met Ala Pro Pro Gln Gln Ala Lys Pro Lys Leu Ile Pro Ala
    1445                1450            1455

Ser Ala Ser Ala Ala Gly Gln
    1460            1465

<210> SEQ ID NO 25
<211> LENGTH: 25
<212> TYPE: DNA
<213> ORGANISM: artificial
<220> FEATURE:
<223> OTHER INFORMATION: phosphorodiamidate morpholino oligonucleotide

<400> SEQUENCE: 25
ggccaaacct cggcttacct gaaat                                          25
```

METHODS FOR DIAGNOSING OR MONITORING MUSCULAR DYSTROPHIES

CROSS-REFERENCE TO RELATED APPLICATION

This application is the U.S. national stage application of International Patent Application No. PCT/EP2015/050372, filed Jan. 9, 2015.

The Sequence Listing for this application is labeled "Seq-List-replace.txt" which was created on Jan. 2, 2019, and is 44 KB. The entire content of the sequence listing is incorporated herein by reference in its entirety.

FIELD OF THE INVENTION

The invention relates to a method for prognosing, diagnosing, determining the risk, and monitoring the evolution of a muscular dystrophy. It also relates to a method for evaluating the efficacy of a treatment of a muscular dystrophy in a subject in need thereof.

BACKGROUND OF THE INVENTION

Muscular dystrophies are devastating neuromuscular diseases. In addition to there being no cure for such diseases, there are no non-invasive methods of diagnosing, prognosing, monitoring or evaluating the efficacy of treatments for such conditions. Currently, fine needle biopsies and serum creatine kinase levels are used. However, muscle biopsies report the state of the muscle only in the site of the biopsy, they are painful, invasive and impractical to perform on a regular basis. Serum creatine kinase levels can vary from day to day in the same patient, making them unreliable indicators of muscle changes under a therapy. In particular, serum creatine kinase would correlate to the degradation of muscle tissue under physical efforts rather than to the pathological state of the patient. For example, it has been shown that the level of this marker decreases as soon as the patient is in a wheel chair.

Therefore, a readily monitored biomarker reflecting the progression of the disease in easily accessible biological fluid is needed.

SUMMARY OF THE INVENTION

Diagnosis of muscular dystrophy has involved the use of serum creatine kinase levels, which are significantly elevated by myopathy or necrosis. Since the serum creatine kinase levels are easily changed with motion or at rest, it has been pointed out that such levels are insufficient for diagnosis or comprehension of disease progression. The present inventors have shown that the presence of a myomesin, or of a fragment thereof, in particular of myomesin 3 or of a fragment thereof, in a biological fluid of a subject is associated to a muscular dystrophy. The presence of a myomesin or of a fragment thereof, in particular myomesin 3 or of a fragment thereof, in a biological fluid of a patient with a muscular dystrophy has never been reported in the prior art. In addition, the results presented herein show that contrary to serum creatine kinase levels, serum myomesin 3 reflects the pathological state rather than functional muscular stimulation. Compared to creatine kinase, myomesin 3, or a fragment thereof, shows lower inter-individual variability and correlated better with the restoration of the dystrophin-associated protein complex and muscle force after pharmaco- or gene therapy treatment of muscular dystrophies.

Accordingly, an object of the present invention is the provision of a novel biomarker associated with the development of a muscular dystrophy, or with the risk of having or developing a muscular dystrophy. It is herein described the use of a myomesin, in particular serum myomesin, more particularly serum myomesin 3, or of a fragment thereof as a biomarker of muscular dystrophies. The invention more particularly relates to a method for diagnosing, prognosing, monitoring the evolution or determining the risk of having or developing a muscular dystrophy, comprising detecting the presence or absence of a myomesin, in particular myomesin 3, or of a fragment thereof in a biological fluid of a subject, the presence of a myomesin, in particular of myomesin 3, or of a fragment thereof being indicative of a muscular dystrophy or of a risk of having or of developing a muscular dystrophy.

With recent progress in pharmaco- or gene therapy for muscular dystrophies there is a growing need for minimally invasive biomarkers that can be used to assess and monitor the efficacy of therapy. Indeed, in order to evaluate the efficiency of a treatment during animal studies, researchers have unlimited access to different types of biopsies or necropsies. In contrast, trials in humans impose ethical restrictions requiring minimally invasive methods to assess and monitor the efficacy of therapy. Thus, a strong need exists in providing reliable and minimally invasive methods for assess and monitor the efficacy of muscular dystrophy therapies. The present inventors herein show that myomesin 3 level, or the level of a fragment thereof, is restored in a biological fluid of (1) mdx mice (animal model of Duchenne muscular dystrophy) after restoration of dystrophin expression using oligonucleotide-mediated exon-skipping and (2) KO-SGCA mice in which α-sarcoglycan expression was stably restored by systemic injection of a viral vector. Therefore, a further object of the invention relates to a method for assessing the efficacy of a treatment of a muscular dystrophy, comprising evaluating the presence or absence of a myomesin, in particular of myomesin 3, or of a fragment of a myomesin such as a fragment of myomesin 3, or evaluating the level of a myomesin, in particular of myomesin 3, or of a fragment thereof (e.g. a fragment of myomesin 3) in a biological fluid. In particular, the method may comprise comparing the level of the myomesin (e.g. myomesin 3) or of the fragment thereof (e.g. a fragment of myomesin 3) to its level in a biological fluid previously collected from the same subject. The evaluated treatment may include, for example, a treatment with a therapeutic agent such as pharmacologic molecules, oligonucleotides and their derivatives such as antisense oligonucleotides and their derivatives (e.g. oligonucleotides mediating exon-skipping of a pre-mRNA of interest) or vectors for gene therapy, or with a therapeutic technique for muscular dystrophy.

The diagnostic method for muscular dystrophy according to the present invention enables early diagnosis and prediction of muscular dystrophy, and it is thus useful for early treatment of muscular dystrophy. In addition, the novel marker according to the present invention is associated with muscular dystrophies, and it can be used for elucidation of the developmental mechanisms of muscular dystrophies and development of therapeutic techniques or agents for the same, in addition to diagnosis and prediction of muscular dystrophy.

The invention further relates to a kit useful for implementing the methods disclosed herein.

DETAILED DESCRIPTION OF THE INVENTION

The present invention provides a novel marker for diagnosis of muscular dystrophies. The level of the marker in biological fluids, in particular in serum and plasma, according to the present invention is low in a normal state and high in the case of muscular dystrophies. Accordingly, the marker is useful for diagnosis intended to determine whether or not a patient carries muscular dystrophy, prediction of the development of muscular dystrophy, screening for a therapeutic agent or technique for muscular dystrophy treatment, evaluation of the efficacy of a therapeutic agent or technique for muscular dystrophy treatment, and other purposes.

According to the present invention, serum myomesin protein, and in particular myomesin 3, is associated to muscular dystrophies, being at very low levels or absent in healthy subjects, but highly present in serum of patients in case of muscular dystrophies.

The myomesin family of proteins comprises closely related structural proteins detected at the M-band of the sarcomere in striated muscles: myomesin-1 (in *Homo sapiens*, UniprotKB/Swiss-Prot accession number P52179—SEQ ID NO:23), myomesin-2 (in *Homo sapiens*, UniprotKB/Swiss-Prot accession number P54296—SEQ ID NO:24) and myomesin-3 (in *Homo sapiens*, UniprotKB/Swiss-Prot accession number Q5VTT5—SEQ ID NO:1). These proteins are involved in sarcomere stability and resistance during intense or sustained stretching (Schoenauer et al., 2008).

In a particular embodiment of the present invention, the detection of a myomesin protein or of a fragment thereof includes the detection of myomesin-1, myomesin-2 or myomesin-3, or of a fragment of myomesin-1, myomesin-2 or myomesin-3.

There has been no report regarding any correlation between these proteins being present in biological fluids and muscular dystrophies.

In a preferred embodiment, the methods of the present invention comprise detecting myomesin-3 or a fragment thereof. The sequence of myomesin 3 is known, and shown in SEQ ID NO:1. In some embodiments, the methods of the invention comprise detecting or quantifying a fragment of myomesin 3. In a particular embodiment, the detected fragment is a C-terminal fragment of myomesin 3, in particular a fragment of about 110 or 140 kDa. In some embodiments, the fragment detected is comprised between amino acids 350 and 1350 of SEQ ID NO:1 or of any natural variant of myomesin 3, for example of corresponding fragments in a sequence presenting at least 90%, preferably 95%, more preferably 99% identity with SEQ ID NO:1. In particular, the fragment detected is comprised between amino acids 355 and 1322 of SEQ ID NO:1 or of any natural variant of myomesin 3, for example of corresponding fragments in a sequence presenting at least 90%, preferably 95%, more preferably 99% identity with SEQ ID NO:1. In a further particular embodiment, the invention implements the detection of a fragment of myomesin 3 comprising amino acids 355-363 (SEQ ID NO:2), 364-380 (SEQ ID NO:3), 461-474 (SEQ ID NO:4), 539-556 (SEQ ID NO:5), 560-567 (SEQ ID NO:6), 577-596 (SEQ ID NO:7), 640-657 (SEQ ID NO:8), 695-713 (SEQ ID NO:9), 761-773 (SEQ ID NO:10), 776-795 (SEQ ID NO:11), 1008-1019 (SEQ ID NO:12), 1076-1086 (SEQ ID NO:13), 1130-1141 (SEQ ID NO:14), 1219-1228 (SEQ ID NO:15) and/or 1303-1322 (SEQ ID NO:16) of myomesin 3 as represented in SEQ ID NO:1, or of any natural variant of myomesin 3, for example of corresponding fragments in a sequence presenting at least 90%, preferably 95%, more preferably 99% identity with SEQ ID NO:1. According to another embodiment, the fragment of myomesin 3 detected according to the invention is selected as a fragment of the whole protein migrating in SDS-PAGE gel at the positions corresponding approximately to 110 or 140 kD.

The terms "biological fluid" include in particular blood, serum, plasma, saliva and urine. According to a particular embodiment of the invention, the biological fluid sample is a serum or plasma sample.

In a particular embodiment, a "muscular dystrophy" or "muscular dystrophies" denote Duchenne muscular dystrophy (DMD), Becker muscular dystrophy (BMD) and limb-girdle muscular dystrophies (LGMD) such as alpha-sarcoglycanopathy (LGMD2D), gamma-sarcoglycanopathy (LGMD2C), calpainopathy (LGMD2A), dysferlinopathy, or Miyoshi muscular dystrophy.

According to the present invention, a "reference sample" may correspond to a biological fluid sample obtained from one or more subjects, preferably two or more, who do not have a muscular dystrophy. The "reference sample" may also correspond to a sample obtained from one or more patients having a muscular dystrophy. In the context of a method for prognosing a patient, for monitoring the evolution of the disease in a patient or for evaluating the efficacy of a treatment of a muscular dystrophy in a patient, the reference sample may in particular be a sample previously collected from said patient, in particular before monitoring or evaluation has started.

The subject of the present invention is a human or non-human mammal. Non-human mammals include in particular a mouse, primate or canine subject. In a preferred embodiment, the subject is a human subject. The subject may present a predisposition to a muscular dystrophy identified thanks to genome analysis, or suspected because of family history. The subject may also suffer from an already established muscular dystrophy. The method of diagnosis of the present invention may also be applied to a subject with no known symptom or predisposition. In some embodiments, the method is applied for mass screening of young children or of newborns. The present invention may also be implemented for detection of myomesin 3 in heterozygous females, for predicting the risk of given birth to a child with a muscular dystrophy. The invention may also be used for monitoring animal models, in particular canine models such as the Golden Retriever muscular dystrophy (GRMD) dog, or mouse models such as the mdx mouse during preclinical evaluation of treatments.

The inventors have also shown that a myomesin, in particular myomesin 3, or a fragment thereof such as a fragment of myomesin 3 is useful for the detection of a muscular dystrophy, or for the determination of a risk of having a muscular dystrophy in young subjects. Accordingly, in a particular embodiment the subject is an adult, an adolescent or a child, in particular a child being of 10 or less than 10 year-old, in particular less than 5 year-old, in particular less than 4 year-old, more particularly a child being 3 year-old or less than 3 year-old. In one embodiment, the subject is a 3- to 10-year old human subject. In an embodiment, the subject is a new born. Accordingly, the detection of a muscular dystrophy or of a risk of having or of developing a muscular dystrophy may be done at an early stage and even before symptoms of the diseases are observed. This marker is also useful in young subjects for predicting the development of muscular dystrophy, screening for a therapeutic agent or technique for muscular dystrophy, evaluation of the efficacy of a therapeutic agent or technique for muscular dystrophy, and other purposes.

In a particular embodiment, the method of the invention is for the diagnosis of a muscular dystrophy, or for determining the risk of having or of developing a muscular dystrophy, comprising detecting the presence or absence of a myomesin, in particular myomesin 3 or of a fragment thereof in a biological fluid sample of a subject, the presence of a myomesin (in particular myomesin 3), or of a fragment thereof being indicative of a muscular dystrophy or of the risk of having or of developing a muscular dystrophy.

The invention aims in particular at detecting the presence or absence of myomesin 3 or of a fragment of myomesin 3 in a serum sample of a subject.

The presence or absence of a myomesin (in particular myomesin 3) or of a fragment thereof may be detected by a number of techniques known in the art for the detection of protein such as:
enzyme-linked immunosorbent assay (ELISA),
lateral flow (immuno)assay,
western-blotting, and
mass spectrometry.

For example, expression of a marker protein in a sample can be determined by immunoassays (immunological assay techniques). Specifically, expression of a marker protein in the sample can be determined based on the reaction between such protein and an antibody that specifically binds thereto. Immunoassays may be carried out in a liquid phase or solid phase, provided that the technique used is conventional in the art. For ease of detection, use of a solid phase may be preferable. In addition, immunoassay techniques are not limited, and immunoassay can be carried out by sandwich assay, competitive assay, Western blotting, or ELISA, as well as a direct solid-phase assay. Any antibody that is able to specifically bind to a myomesin, in particular myomesin 3, or to a fragment thereof, and more particularly to a C-terminal fragment of myomesin 3 may be used in immunoassays according to the invention. In some embodiments, the fragment detected is comprised between amino acids 350 and 1350 of SEQ ID NO:1 as provided above (the fragment being in particular a sequence comprising or consisting of one or more of SEQ ID NO: 2 to SEQ ID NO:16) or of any natural variant of myomesin 3. The antibody may be a monoclonal or polyclonal antibody. Alternatively, it may be, for example, a Fab or Fv fragment capable of binding to an epitope of a marker protein. When a primary antibody and a secondary antibody are used, both may be monoclonal antibodies. Alternatively, either the primary or secondary antibody may be a polyclonal antibody. An antibody can be prepared by a method known in the art, or a commercially available antibody may be used such as the anti-myomesin 3 antibody from Proteintech which is a polyclonal rabbit antibody against the C-terminal 325 amino acids of myomesin 3 or a commercially available antibody may be used such as the anti-myomesin 2 from Santa Cruz (myomesin-2 antibody (H-65): sc-50435) against amino acids 913-977 mapping within an internal region of myomesin-2 of human origin.

Alternatively, the expression of a marker protein can be determined by mass spectrometry (MS) and comprises the identification of proteins by measuring the ratio between mass and charge (m/z) of peptides obtained from their enzymatic digestion (MS) or of their fragments (MS/MS). The m/z of thus generated peptides are then compared to the calculated m/z of protein sequences present in databases permitting the protein identification. According to a particular embodiment, the multiple reaction monitoring (MRM) approach can be used in the present invention, in order to allow quantitative and/or qualitative detection of the peptides in biological fluids.

According to another aspect, the invention relates to a method for monitoring a muscular dystrophy progression. In this case, the method may comprise the step of quantifying the level of a myomesin, in particular myomesin 3, or of fragments thereof at a T1 time in the subject, a level higher at a time T2 following T1 being indicative of a disease progression and a lower or equal expression at T2 being indicative of a remission or stabilization. The evolution of the level of myomesin or of a fragment thereof, in particular myomesin 3 or myomesin 3 fragment level may also be compared to a reference sample from a patient of an equivalent age having a muscular dystrophy.

According to a further aspect, the invention relates to a method for determining the efficacy of a treatment of muscular dystrophy. In this case, the method may comprise the step of quantifying the level of the myomesin protein (e.g. myomesin 3) or of a fragment thereof at a T1 time in the subject, a level lower at a time T2 following T1 being indicative of an efficient treatment while an increased or equal expression at T2 being indicative of an inefficient treatment or less efficient treatment. The evolution of the myomesin (e.g. myomesin 3) or myomesin fragment (e.g. myomesin 3 fragment) level may also be compared to a reference sample from a patient of an equivalent age having a muscular dystrophy. A lower level in the subject than in the reference sample is indicative of an efficient treatment of the muscular dystrophy.

By "higher expression level" or "lower expression level" is meant an expression level the variation of which is significant, according to methods well known by those skilled in the art.

Both methods of monitoring a muscular dystrophy progression and of determining the efficacy of a treatment of muscular dystrophy may involve the use of a quantitative method for determine the level of a myomesin protein (e.g. myomesin 3) or of a fragment thereof, such as ELISA or MRM mass spectrometry. In addition, both methods include the collection of samples at different times (for example the collections are made several days/weeks/months away). In addition, in the method for determining the efficacy of a treatment, the first and second samples may be collected both after the treatment has been provided to the patient (for example, the first sample is collected after the treatment, the same day as the treatment or several days/weeks/months after the treatment, and the second sample is collected several days/weeks/months after collection of the first sample).

Differential expression of different myomesins in muscle fibres (MYOM3 was found mainly in intermediate speed fibres (type IIa) of skeletal muscle, while fast fibres express more MYOM2 and MYOM1 is expressed in all muscle fibres (Schoenauer et al, 2008)) implies a possibility to follow the results of therapeutic treatment for each type of muscle fibres. Accordingly, the invention also provides a method for following the outcome of a therapeutic treatment of a muscular dystrophy, comprising detecting the absence or the presence, and/or the level of at least one myomesin protein selected from myomesin 1, myomesin 2 and myomesin 3 in a biological fluid of a subject, in particular detecting the absence of presence of all three proteins, to thereby determine the impact of the treatment on each type of muscle fibres.

Furthermore, the diagnostic, prognosis, monitoring, determination of the risk of having or of developing the disease or the determination of the efficacy of the treatment may be confirmed in a further step by methods known in the art for the evaluation of muscular dystrophies, such as by determining serum creatine kinase levels, by searching specific markers in muscular biopsies, etc.

Another aspect of the invention relates to a kit for the diagnosis, prognosis, monitoring or determination of the risk of having or of developing a muscular dystrophy or the determination of the efficacy of a treatment of a muscular dystrophy, comprising means for detecting or dosing a myomesin protein, in particular of myomesin 3, or a fragment thereof in a biological fluid sample from a subject. In a particular embodiment, the kit comprises means for implementing an ELISA or Western-blot analysis. For example the kit comprises a specific means for detecting a myomesin protein, such as myomesin 3, or a fragment thereof, such as an antibody as described above. The kit may also comprise instructions for carrying out the method of the invention.

According to another aspect, the invention also provides a methods for the diagnostic or the prognosis of a muscular dystrophy, for monitoring such a muscular dystrophy, for determining the risk of having or of developing a muscular dystrophy, or for determining the efficacy of a treatment against a muscular dystrophy, comprising detecting in a biological fluid of a subject the absence or the presence of at least one protein selected from those listed in tables 2 and 3 of the examples presented below.

The present invention will now be described with reference to the following figures and examples.

LEGENDS OF THE FIGURES

FIG. 1: Analysis of Myomesin 3 in sera from healthy subjects and DMD patients by Western blot. Antibodies against C-ter part of myomesin-3 revealed the presence of both 140 kDa and 110 kDa fragments exclusively in serum samples from DMD patients which correlates with the mass spectrometry LC/MS/MS analysis.

Figure 2:
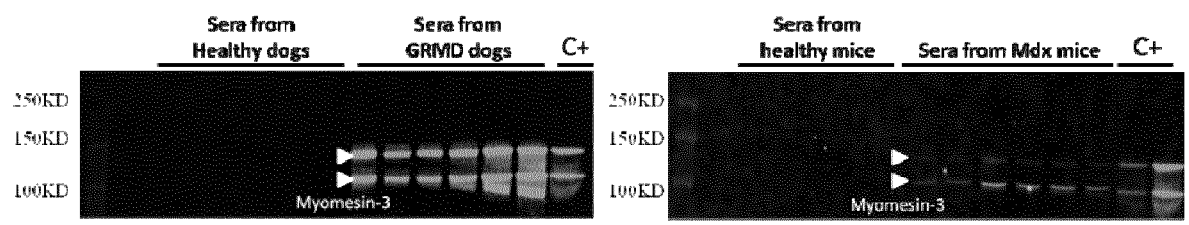

FIG. 2: Analysis of Myomesin 3 in sera from dogs and mice by Western blot. Western blot analysis of sera from animal models of DMD (GRMD dog and mdx mouse) revealed the presence of the myomesin-3 exclusively in sera from the affected animals.

Figure 3:
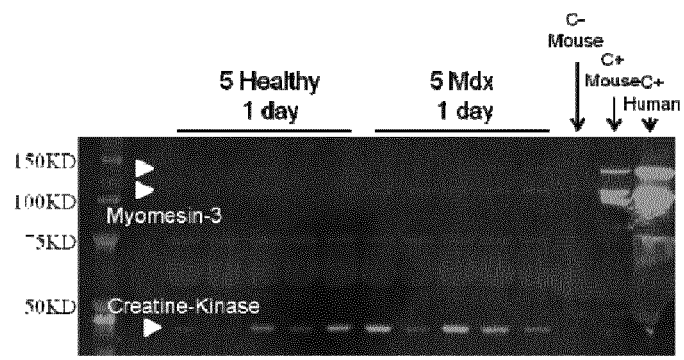

FIG. 3: Analysis of Myomesin 3 and CK in sera from 1 day-old healthy and mdx mice by Western blot. Serum from 5 healthy and 5 mdx mice was used in this experiment. Myomesin-3 fragments are detectable at the low level in all of the five mdx tested. Importantly, there is no correlation between CK level and Myomesin 3 level in the studied animals: CK was detected in all samples while myomesin 3 only in mdx mice. Moreover, some healthy mice demonstrated higher CK level compared to those in "low level CK" mdx mice (see healthy mice 3 and 5 and mdx mice 2 and 5).

Figure 4:
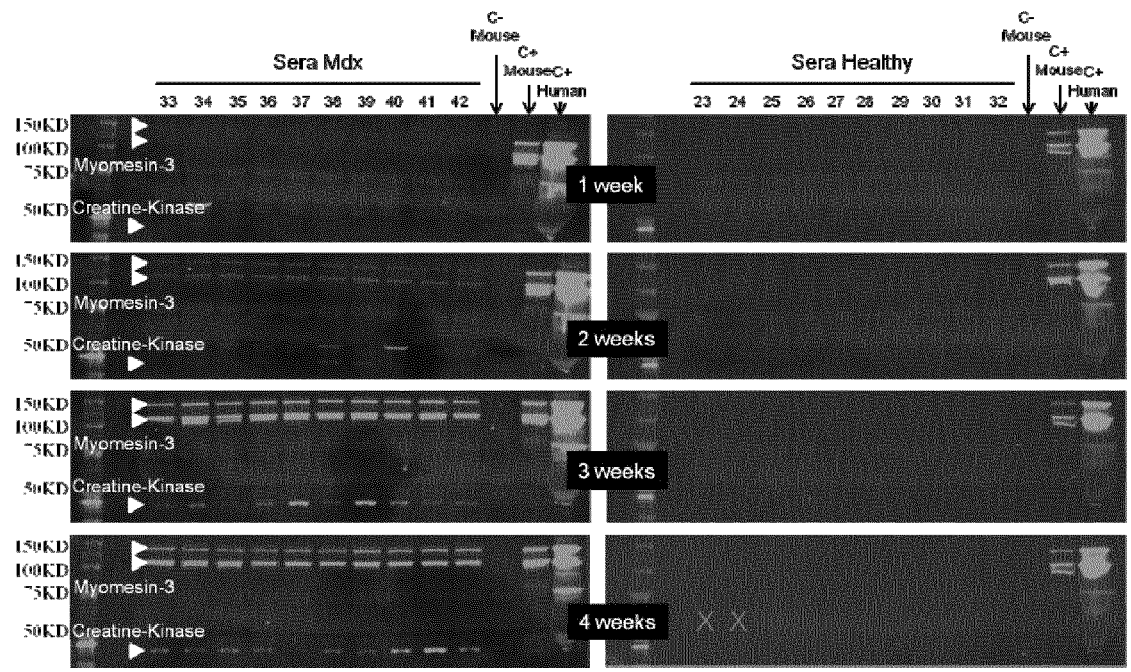

FIG. 4: Analysis of Myomesin 3 and CK in sera from mdx and healthy mice at different ages by Western blot. Analysis of MYOM3 and creatine kinase was performed by Western blot on sera from 10 healthy controls and 10 mdx mice. Samples were taken each week starting from 1-week of age. Gray crosses indicate that there was no serum available for these mice.

Figure 5:
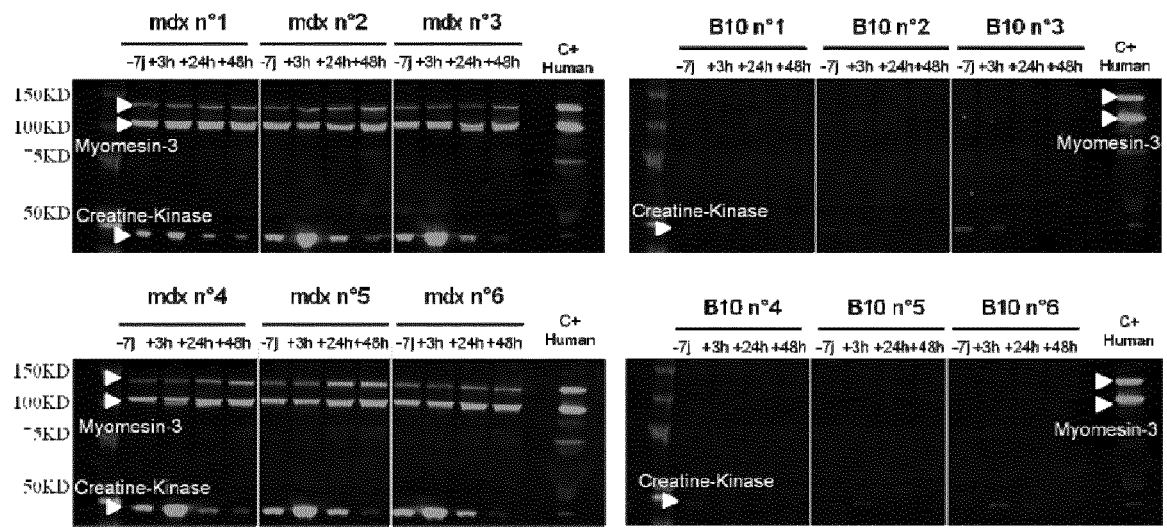

FIG. 5: Constant level of Myomesin 3 and variable level of CK in sera from mdx and healthy mice after physical exercise. Analysis of MYOM3 and creatine kinase was performed by Western blot on sera from two groups of mice (healthy controls and mdx). Six 3 month-old mice were subjected to an intense physical exercise on a homemade treadmill. Serum samples were collected 7 days before exercise and 3 h, 24 h, 48 h after exercise.

Figure 6:
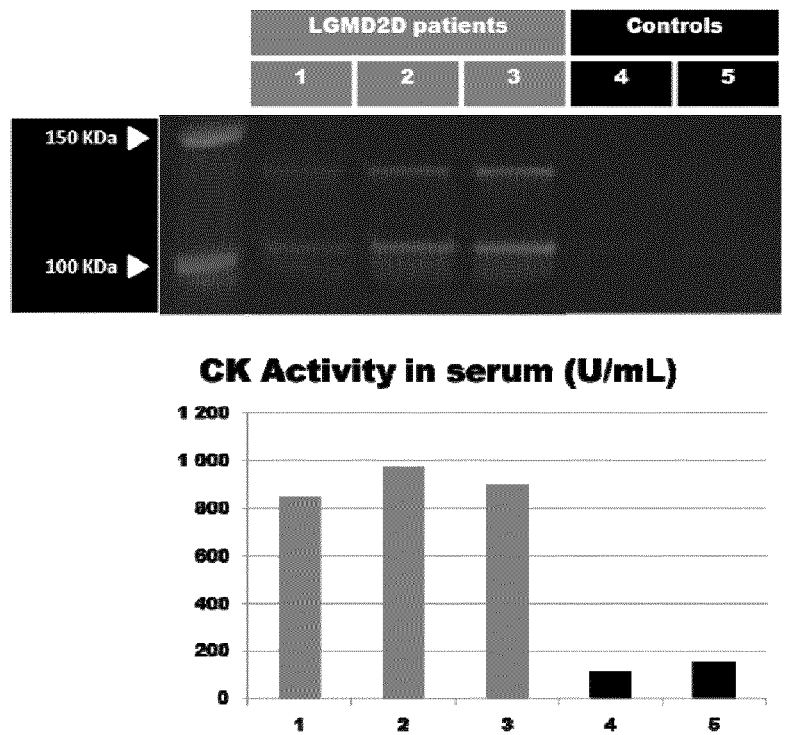

FIG. 6: MYOM3 fragments in sera of LGMD2D patients. Upper panel: Western blot analysis of MYOM3 in serum from LGMD2 patients (1-3) and controls (4-5). Lower panel: CK assays on the same sera. The activity was measured in international system unit per liter (U/L).

Figure 7:
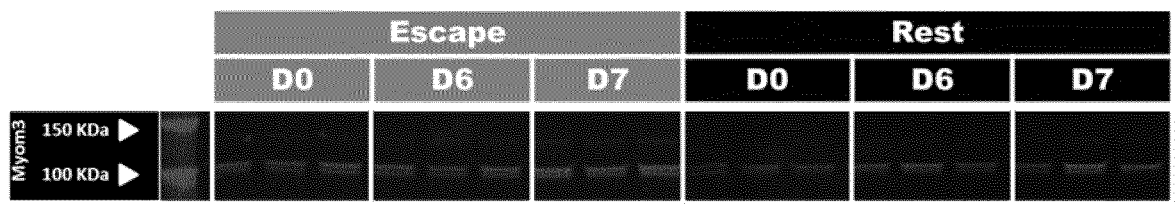

FIG. 7: Constant level of MYOM3 fragments in serum of KO-Sgca mice after physical exercise. Western blot analysis of MYOM3 in sera from a group of KO-Sgca mice at different time of the Escape test ("Escape") (D0: 6 days before the exercise, D6: 20 min after the exercise, and D7: 24 hours after exercise). "Rest": the same time points for the control group of mice not subjected to physical exercise (n=3). The level of the MYOM3 stays stable at any time point.

Figure 8:
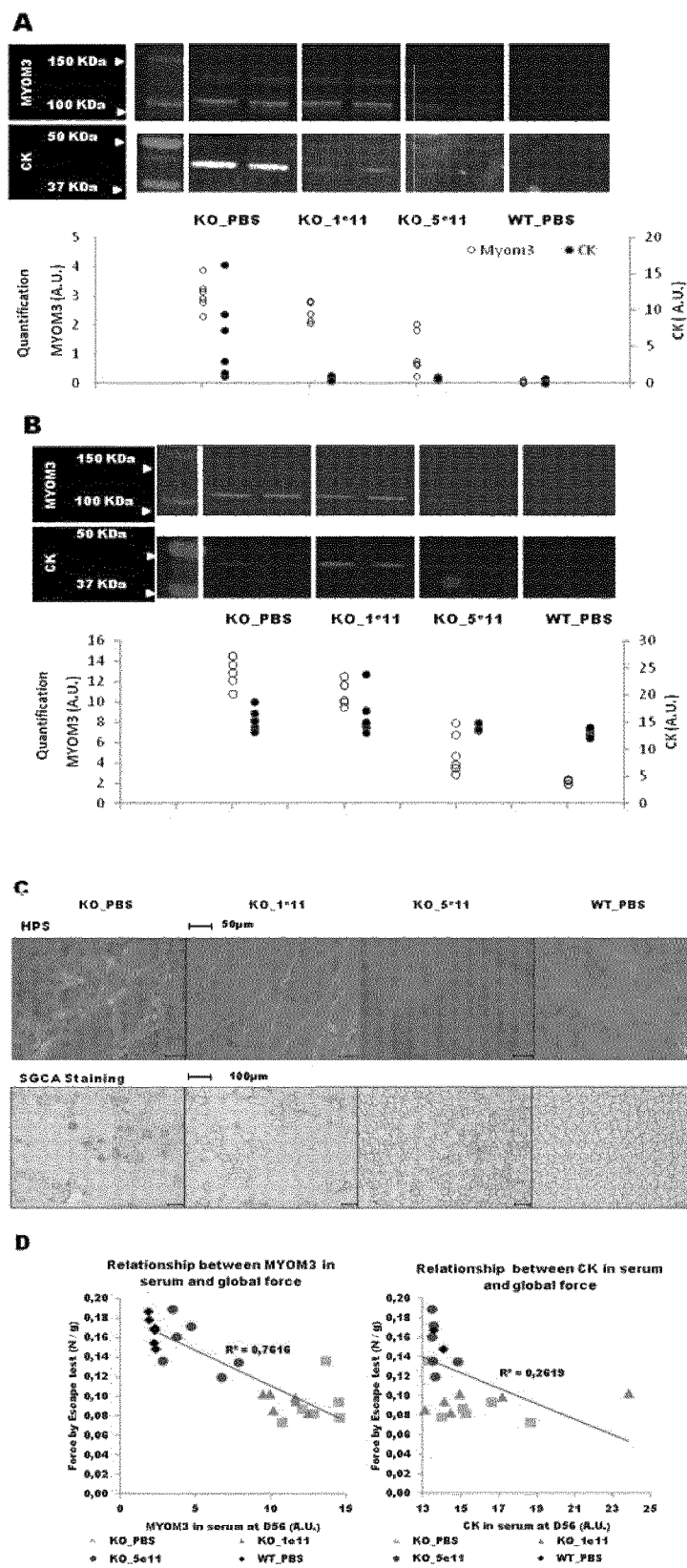

FIG. 8: Gene therapy of KO-Sgca mice decreases the level of MYOM3 fragments in serum. Mice were systemically injected either with PBS or with 1e11vg or 5e11vg of rAAV coding for wt human alpha-sarcoglycan (n=6 for each group), At days $14^{th}$ and $56^{th}$ after injections serum was taken for the analysis of CK and MYOM3. Before the endpoint of the experiment (56 days after injection, at age of 90 days) muscle force was estimated by the escape test. At the end point mice were sacrificed and gastrocnemius anterior muscle transverse sections were characterized by HPS staining and the presence of SGCA were analysed with antibody against SGCA. A: Upper panel: Western blot analysis of MYOM3 and CK 14 days after rAAV treatment. Two representative analyses are presented for each group. Lover panel: Graph representation of the MYOM3 and CK level in each group 14 days after rAAV treatment. Each spot on the graph correspond to one animal. B: Upper panel: Western blot analysis of MYOM3 and CK 56 day after rAAV treatment. Two representative analyses are presented for each group. Lower panel: Graph representation of the MYOM3 and CK level in each group 56 days after rAAV treatment. Each spot on the graph correspond to one animal. C: Histochemical characterization of gastrocnemius anterior muscles from treated and control mice 90 days after rAAV injection. D: Correlation between the serum level of MYOM3 fragments and muscle force after gene therapy treatment. Plots show relationships between MYOM3 and muscle force and between CK and muscle force. The level of MYOM3 fragments are in a good correlation with the restoration of the muscle morphology and physical force.

Figures 9, 10:
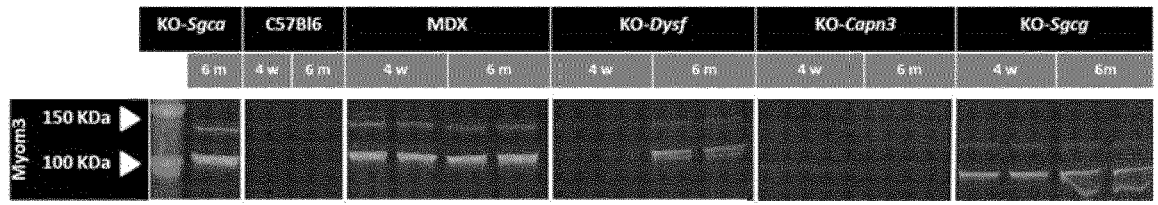

FIG. 9: MYOM3 fragments in serum of other muscular diseases. Analysis of MYOM3 was performed by Western blot in sera from mice models for different dystrophies (KO-Sgca, MDX, KO-Dysf, KO-Capn3 and KO-Sgcg) and controls (C57Bl6) at the age of 4 weeks and 6 months. The high level of MYOM3 fragments were found at the both ages in MDX, KO-Sgca and KO-Sgcg mice while in KO-Dysf these fragments were barely detectable at 1 month age and reached its maximum at the age of 6 month. Only a faint labelling of MYOM3 fragment was detected in KO-Capn3 mice.

FIG. 10: List of Myomesin-3 peptides identified by mass spectrometry in sera from 4 DMD patients (SEQ ID NOs: 2-16, respectively). Only peptides with an ion score higher than 30 at least in one DMD patient are shown.

Figure 11:
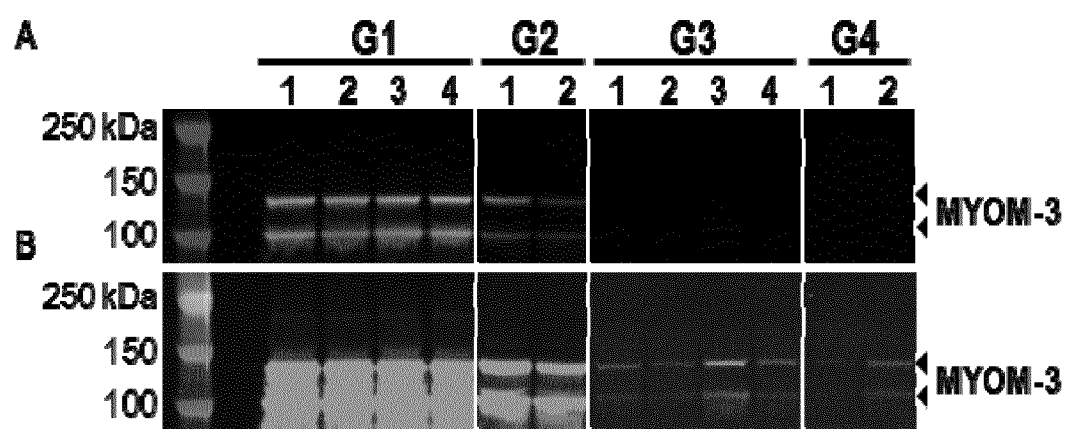

FIG. 11. Western blot analysis of MYOM3 in sera from subgroups of young (G1) and older (G3) DMD patients as well as young (G3) and older (G4) healthy subjects. A: normal exposure; B: boosted exposure. For explanation of groups and subgroups see Table 1. Fifty micrograms of serum proteins was loaded in each well.

Figure 12:
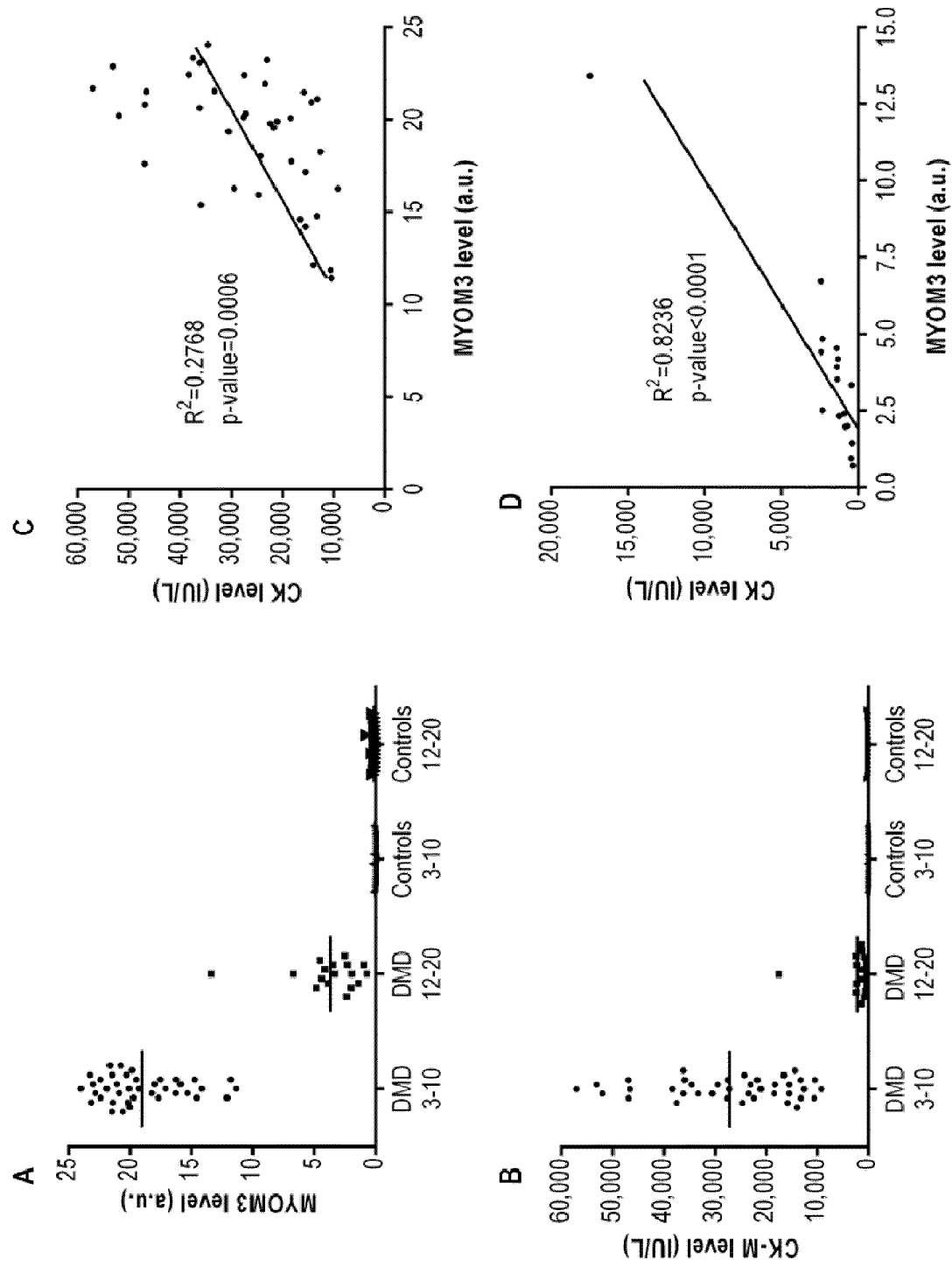

FIG. 12. Expression levels of serum MYOM3 fragments (A) and CK (B) in sera from the entire US cohort including 39 young and 17 older DMD patients as well as 29 young and 18 older healthy controls. To measure levels of the MYOM3 fragments, 50 µg of serum proteins were analysed by Western blot, then band intensities were quantified and expressed in arbitrary units (a.u). The CK enzyme activity in serum is expressed in international units per litre (IU/L). (C) Linear regression analysis between serum levels of the MYOM3 fragments and CK for young patients. (D) Linear regression analysis between serum levels of the MYOM3 fragments and CK for older DMD patients.

Figure 13:
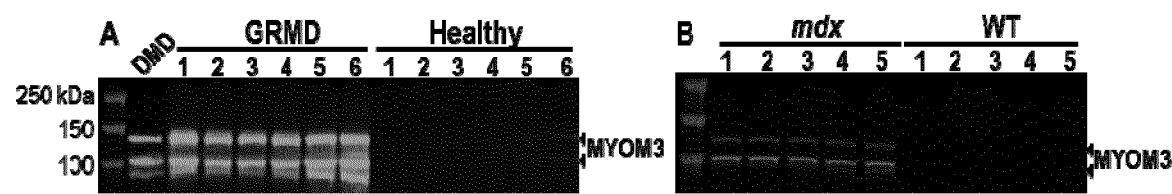

FIG. 13. MYOM3 fragments are specifically present in sera from animal models of DMD. A: Western Blot analysis of serum from GRMD and healthy dogs. GRMD #1-4: two month old; #5-6: 18 months old. Healthy #1-4: two months old; #5-6: 18 months old dogs. DMD: control serum from DMD patient. B: Western Blot analysis of serum from 6 months old mdx and WT mice. WT: C57/BL10 strain.

Figure 14:
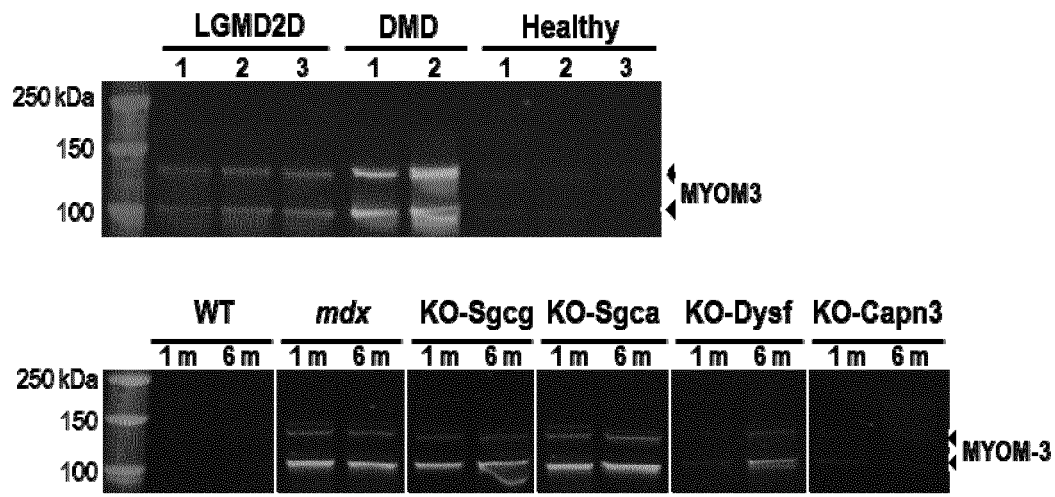

FIG. 14. A: Western blot analysis of the MYOM3 fragments in serum from 3 LGMD2D patients (#1 is 35, #2 is 23 and #3 is 24 years old). Serum from 2 DMD patients (group G1) and 3 healthy individuals (group G4) were used as controls. B: Western blot analysis of the MYOM3 fragments in serum from mouse models of different muscular dystrophies at 1 and 6 months of age. WT: C57BL/6J mouse; mdx (model for DMD); KO-Sgcg: model for LGMD2C; KO-Sgca: model for LGMD2D; KO-Dysf: model for LGMD2B; KO-Capn3: model for LGMD2A.

Figure 15:
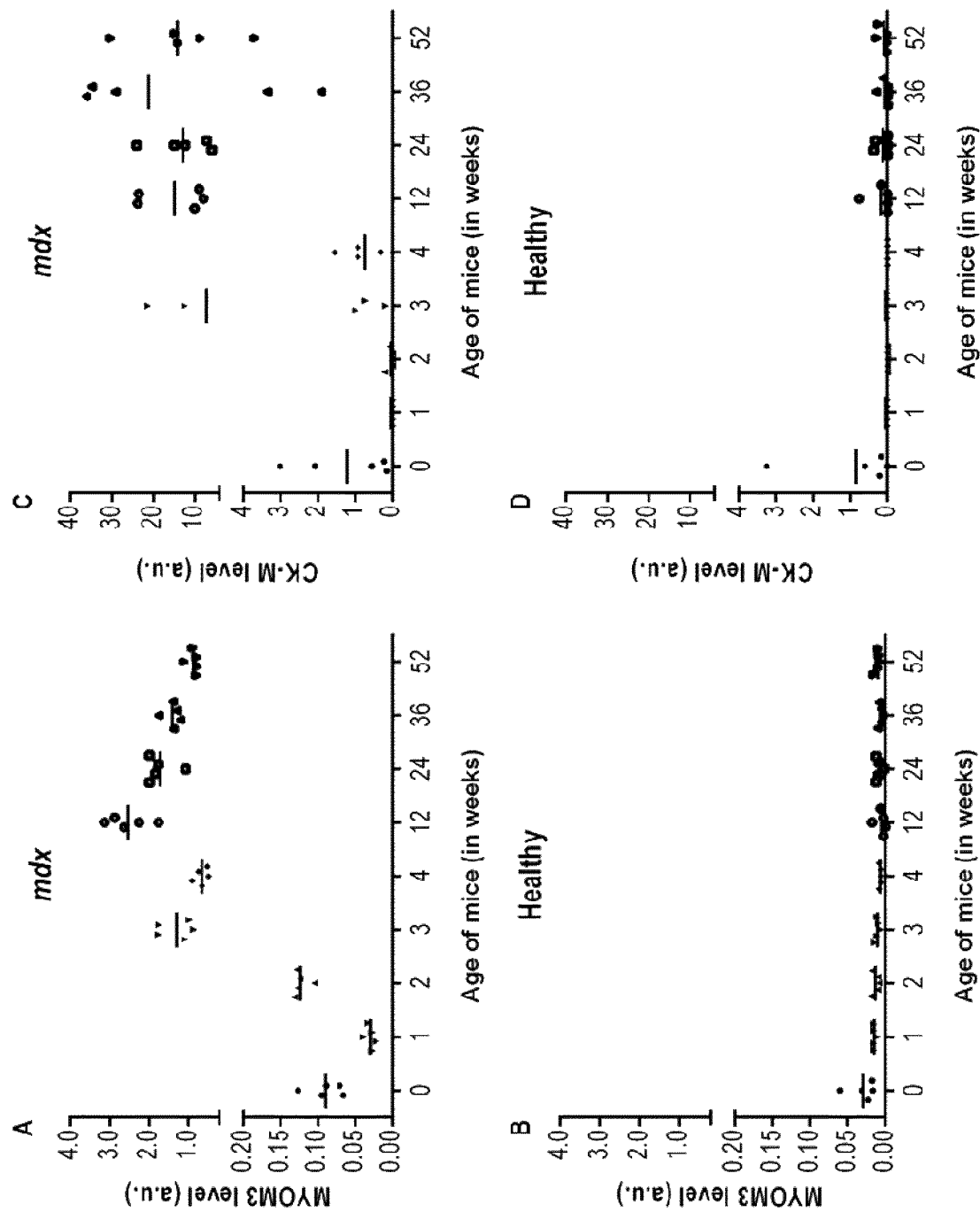
Figure 20:
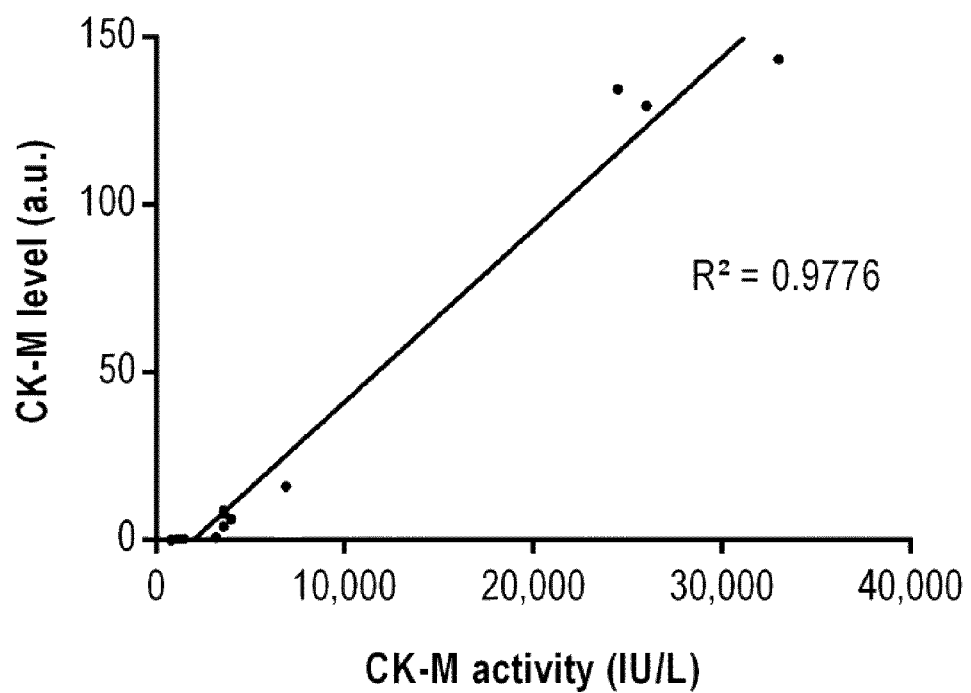

FIG. 15. Levels of the MYOM3 fragments (A, B) and CK-M (C, D) in serum from healthy (B, D) and mdx (A, C) mice at different ages as estimated by Western blot analysis. Intensity of the bands (in arbitrary units, a.u.) on different gels was normalised by the respective bands of the positive control (50 µg of serum proteins from the same mdx mouse present on each gel). Fifty micrograms of serum proteins was used for the analysis. Age 0 corresponds to newborn mice. Estimation of the CK-M level by Western blot analysis correlated well with the CK activity (FIG. 20).

Figure 16:
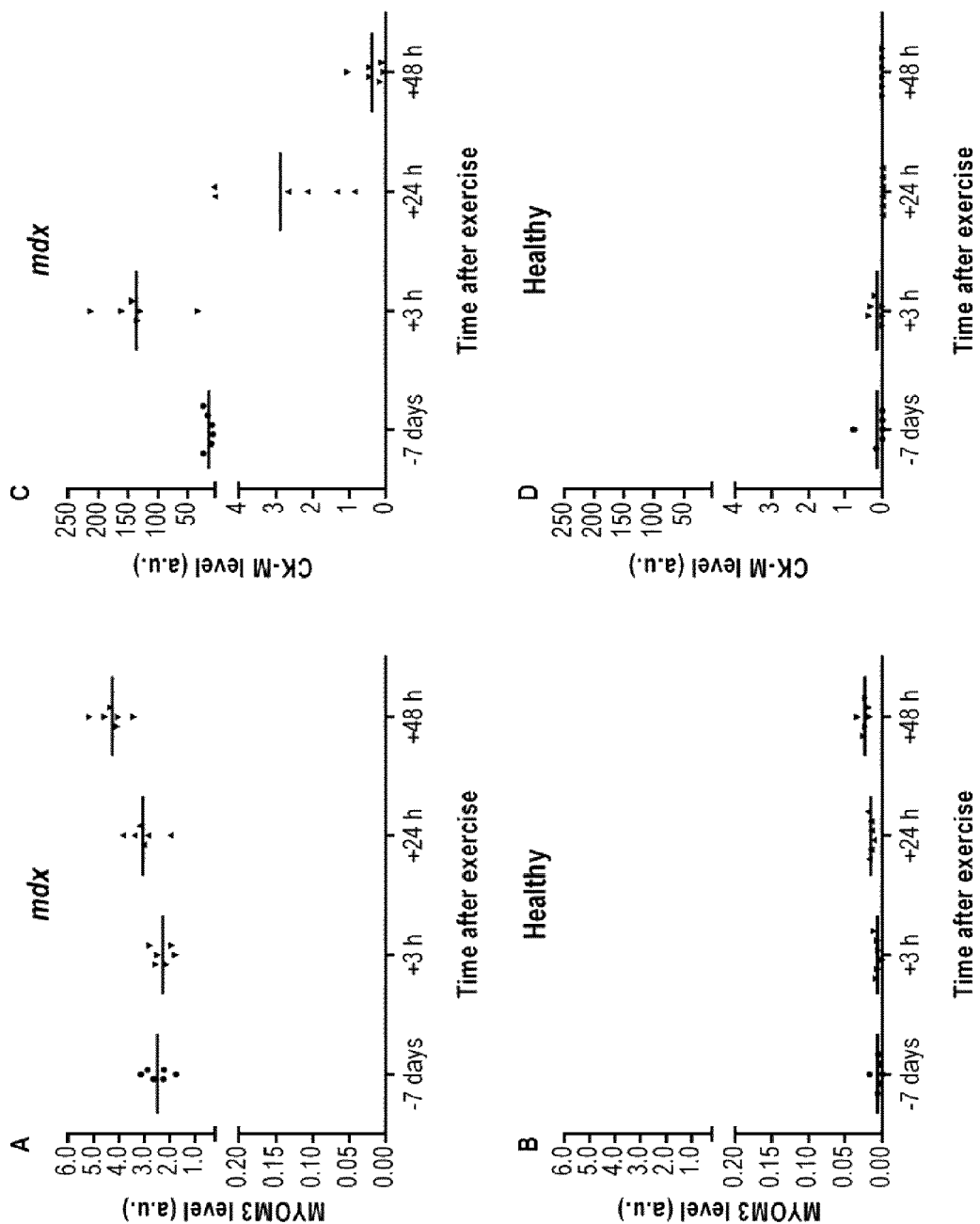

FIG. 16. Levels of the MYOM3 fragments (A, B) and CK-M (C, D) in serum from healthy (B, D) and mdx (A, C) mice at different time after physical exercise estimated by Western blot analysis. Band intensity on different gels was normalised by the respective bands of the positive control (50 µg of serum proteins from the same mdx mouse present on each gel). Fifty micrograms of mouse serum was used for the analysis.

Figure 17:
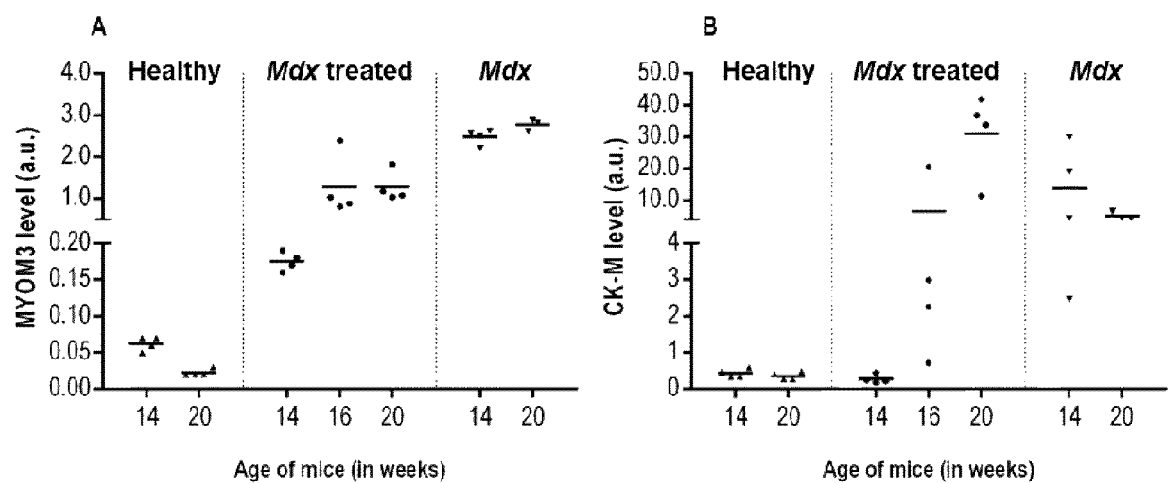

FIG. 17. Effect of antisense oligonucleotide-mediated exon skipping therapy in mdx mice on the serum levels of the MYOM3 fragments and CK-M. Four 12 weeks aged mdx mice received a single 12.5 mg/kg tail vein injection of Pip6a-PMO. Blood samples from the injected mdx mice were collected at 14, 16 and 20 weeks of age (2, 4 and 8 weeks post-injection) and from the control mice at 14 and 20 weeks of age. Levels of the MYOM3 fragments and CK-M were estimated by Western blot analysis.

Figure 18:
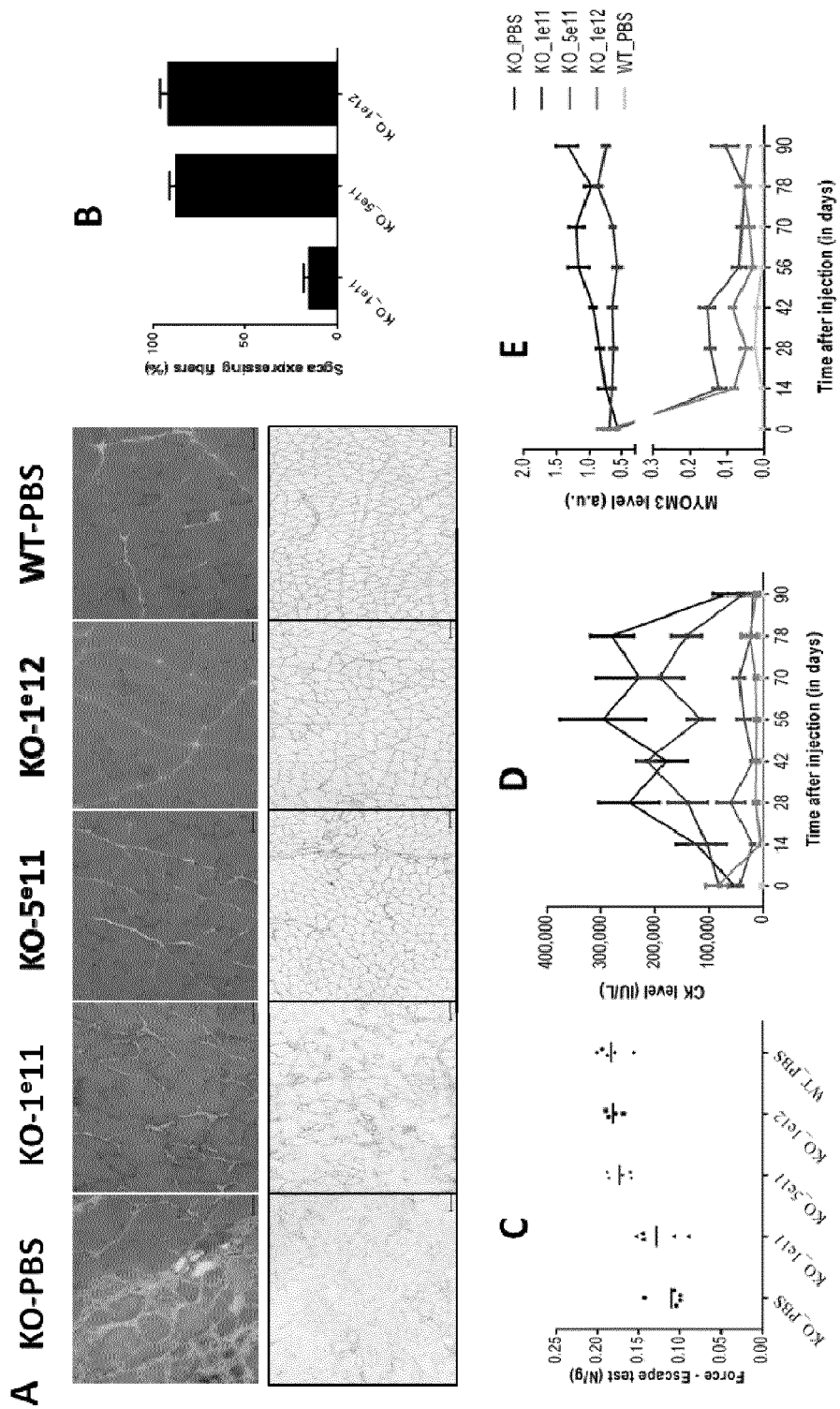

FIG. 18. Comparison of different assays for the follow up of the gene therapy treatment in KO-Sgca mice. A: Histological analyses (upper panel: Hematoxylin Phloxine Saffron stain; lower panel: immunodetection of α-sarcoglycan) of gastrocnemius muscles after treatment with increasing doses of rAAV coding for huSgca (1e11, 5e11, and 1e12 vg). B: Quantitative analysis of α-sarcoglycan positive fibres after the treatments. C: Restoration of muscular strength (escape test) 83 days after the treatment. D: Serum CK and E: MYOM3 fragments levels at different time after the treatment (mean±SEM). F: Raw P-values (Student's t test) for the comparison of MYOM3 and CK levels between different groups of mice at different time points. The values below the threshold 0.01 are in pink, and below 0.05 are in yellow. KO_PBS, KO_1e11, KO_5e11, KO_1e12: KO-Sgca mice injected with PBS or the respective dose of the vector. WT_PBS: C57BL/6J control mice injected with PBS. Levels of the MYOM3 fragments and CK-M were estimated biweekly by Western blot analysis.

Figure 19:
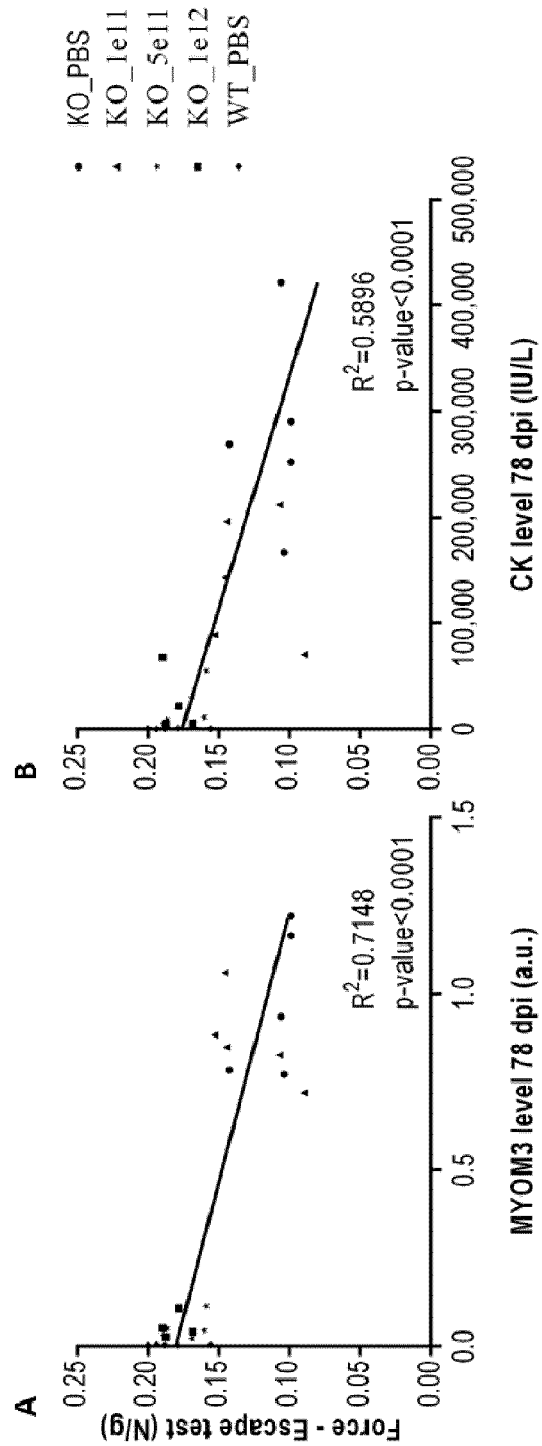

FIG. 19: Correlation between the levels of the MYOM3 fragments (A) or CK-M (B) in serum with muscle force evaluated by the escape test. KO_PBS, KO_1e11, KO_5e11, KO_1e12: KO-Sgca mice injected with PBS or the respective dose of the vector. WT_PBS: C57BL/6J control mice injected with PBS. Levels of the MYOM3 fragments and CK-M were estimated by Western blot analysis 78 days post-injection. Dpi: days post-injection.

FIG. 20: Correlation between the CK-M measured by Western blot (a.u) and its enzymatic activity (IU/L). Level of CK was measured by two methods in serum of mdx mice before and at different time after physical exercises. Three mice and four time points were used to build the graph.

Figure 21:
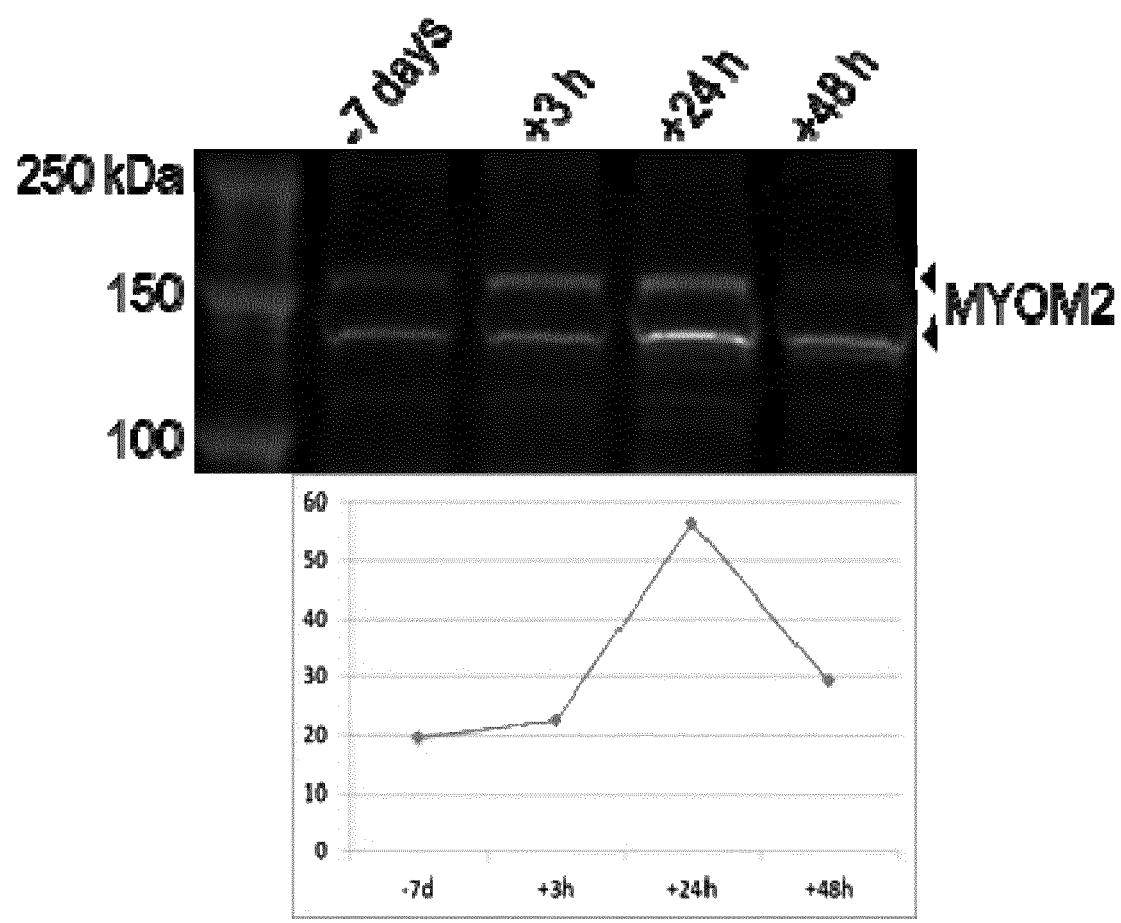

FIG. 21: Effect of physical exercise on the level of the MYOM2 fragments in serum from mdx mice. Serum samples were taken 7 days before and 3, 24 and 48 hours after the exercise. Upper panel: Western blot analysis with anti-Myom2 antibodies; lower panel: quantification of the myom2 expression. MYOM2: position of the myom2 fragments. One microliter of serum was used for the analysis.

EXAMPLES

Example 1

Material and Methods

Serum Depletion

Using the manufacturer instructions, 10 microliters of serum (6 healthy donors and 4 DMD patients) were depleted with an affinity depletion column that selectively removes 12 of the most abundant proteins ("Proteome purify 12" kit from R&D System). Then, 300 µl of depleted solution was precipitated with 4 volumes of acetone 100% overnight at 4° C. followed by centrifugation at 14000 g for 10 minutes at 4° C. The pellet was resuspended in 50 µl buffer containing 6M urea/2M thiourea and protein concentration was determined by Bradford assay.

Mass Spectrometry (LC-MS/MS) Analysis

A volume of serum containing ten micrograms of proteins was adjusted to 120 µl of the reaction mixture containing 4 M urea, 1.5 M thiourea and 50 mM tris-HCl pH 8.3. Proteins were reduced with 10 mM dithiothreitol for 30 min and then alkylated with 55 mM iodoacetamide for 20 min. Alkylated proteins were digested firstly with 500 ng of endopeptidase lys-C (Wako) for 3 h at room temperature (RT). Then, the mixture was diluted with 3 volumes of MilliQ-water and treated with 500 ng of trypsin (Sequence Grade Trypsin, Promega) for 16 h at RT. Enzymatic activity was stopped by addition of formic acid to a final concentration of 3%. Samples were stored at −20° C. until use.

Peptide mixture was desalted using ZipTip$_{\mu-C18}$ Pipette Tip (Millipore) and separated with an Easy nano-LC Proxeon system (Thermo Fisher Scientific) equipped with a reversed phase C18 column (Easy-Column Proxeon C18, L 10 cm, ID 75 µm, 120 Å) with the following parameters: 300 nl/min flow, gradient rising from 95% solvent A (0.1% formic acid) to 25% B (100% acetonitrile, 0.1% formic acid) in 20 min, then to 45% B in 40 min and finally to 80% B in 10 min. Eluates were monitored by a LTQ Velos Orbitrap mass spectrometer (Thermo Fisher Scientific) in full ion scan mode at a resolution of 30,000 and a mass range of 400-1,800 m/z. The mass spectrometer was operated in a data dependent manner, selecting the 20 most intense precursor ions with a dynamic exclusion of 15 sec (isolation width of 1 Da and activation of 0.250 for 10 ms) for sequential fragmentation by collision induced dissociation (collisional energy of 40%).

Data were processed with Proteome Discoverer 1.4 software (Thermo Fisher scientific) coupled to an in house Mascot search server (Matrix Science, 2.3.2 version) using SwissProt database and the following parameters: human/mouse/dog species, mass tolerance of 10 ppm for precursor ions or 0.6 Da for fragments, and two missed cleavage site. Partial chemical modification such as oxidation of methionine and carbamidomethylation of cysteine were taken into consideration for the queries. False discovery rate was estimated using a reversed database search approach.

Vector Construction and Production

A plasmid carrying the coding sequence of human α-sarcoglycan was obtained from Dr. Jeng-Shin Lee (HGTI, Harvard). It was used to construct the pAAV.Des. SGCA 142T plasmids that consist of an AAV-based pSMD2-derived vector (Snyder, 1997) where the human α-sarcoglycan is placed under the control of a human Desmin promoter and 4 repeats of the miR-142-3p target sequences described in (Brown et al., 2006). Plasmids were prepared using the Nucleobond PC2000EF kit from Macherey-Nagel (Germany). The integrity of the constructs was confirmed by sequencing. Adenovirus free AAV2/8 viral preparations were generated by packaging AAV2-ITR recombinant genomes in AAV8 capsids using a three plasmid transfection protocol (Bartoli, 2006). After DNA extraction by successive treatments with DNAse I and proteinase K, viral genomes were quantified by a TaqMan real-time PCR assay using primers and probes corresponding to the ITR region and to the albumin gene (Alb) for normalization of the data across samples. The primer pairs and TaqMan MGB probes used for ITR amplification were: 1AAV65/Fwd: $_5$CTCCAT-CACTAGGGGTTCCTTGTA$_3$, (SEQ ID NO:17), 64AAV65/rev: $_5$TGGCTACGTAGATAAGTAGCATGGC$_3$, (SEQ ID NO:18) and AAV65MGB/taq: $_5$GTTAATGAT-TAACCC$_3$, (SEQ ID NO:19). The primer pairs and TaqMan MGB probes used for Alb amplification were: ALB.Fwd: $_5$GCTGTCATCTCTTGTGGGCTGT$_3$, (SEQ ID NO:20), ALB.Rev: $_5$ACTCATGGGAGCTGCTGGTTC$_3$, (SEQ ID NO:21) and AlbVic/taq: 5'CCTGTCATGCC-CACACAAATCTCTCC$_3$, (SEQ ID NO:22).

Animal Models, Blood Sampling and Vector Administration

The mouse strains included in this study are shown in Table 1. All animal procedures were performed in accordance with the directive of 24 Nov. 1986 (86/609/EEC) of the Council of the European Communities and were approved by Genethon's ethics committee under the number CE12-034. C57BL/6 mice were purchased from Charles River Laboratories (Les Oncins, France). Sgca_null (KO-Sgca) mice were obtained and bred at Généthon's animal facility. Mice were handled according to A1 biosafety requirements in accordance with the European guidelines for use of experimental animals. All experiments were performed accordingly to minimize animal discomfort. Prior to blood extraction, mice were anesthetized by intraperitoneal injection of ketamine/xylazine. Anesthetized mice were sacrifice by cervical elongation at the end of the experiments.

All experimental gene transfer protocols were performed on 4 week-old male mice. Systemic administrations were performed by tail vein injections of 500 μl of solution containing different quantities of rAAV (1e11 or 5e11 viral genome(vg)/mouse) or Phosphate-Buffered Saline (PBS; Gibco, Life Technologies). Samples were taken for the analysis at $14^{th}$ and $56^{th}$ days after injection. Blood was collected by retro-orbital puncture of anesthetized animals.

TABLE 1

Principal features of mouse strains of muscular dystrophy models

| Name | Official name | Mutation | reference | Localisation |
|---|---|---|---|---|
| KO-Capn3 | B6-Capn3$^{tm2.1Gnt}$ | KO-CAPN3 partial out-of-frame deletion | Laure, et al.; FEBS J. 2009 | GNT |
| KO-Dysf | B6.A-Dysf$^{prmd}$/J | insertion transposon | Lostal, et al.; Hum Mol Genet. 2010 | GNT |
| KI-FKRP | B6; 129-FKRP$^{tm1Gnt}$ | KI-FKRP L276I | | Cerfe |
| KO-Sgca | B6-Sgca$^{tm1Kcam}$ | KO-SGCA partial out-of-frame deletion | Duclos, et al; J Cell Biol. 1998 | GNT |
| KO-Sgcg | B6-Sgca$^{tm1Kcam}$ | KO-SGCG partial out-of-frame deletion | Hack AA, et al; J Cell Biol. 1998 | GNT |
| MDX | B6Ros.Cg-Dmd$^{mdx-4Cv}$/J | C-to-T transition at position 7916 (DYS exon 53) | Chapman VM, et al; PNAS. 1989 | Charles River Laboratories |
| WT | C57Bl/6 | | | Charles River Laboratories |

Physical Exercise

Two groups (healthy controls and mdx) of six 3 month-old mice were placed on a homemade treadmill to run with a downstairs inclination of 15° at the speed of 8 m/min for 5 min, followed by 12 m/min for 25 min. Serum samples were collected 7 days before exercise and 3 h, 24 h, 48 h after exercise and stored at −80° C.

Aging

Serum samples of 10 healthy controls and 10 mdx mice from 1-week up to 4-week-old were collected each week and stored at −80° C. Serum samples from 1 day-old mice (5 healthy controls or 5 mdx) were collected after euthanasia.

Escape Test

Mouse muscle force was evaluated by the "escape test" (Carlson, 1990). Mice were placed on a platform facing the entrance of a tube that was 30 cm long. A cuff was wrapped around the tail and connected to a fixed force transducer. In response to gentle pinching of the tail, mice tried to escape within the tube. This was prevented by attaching the tail to the force transducer and a short peak of force was recorded. Maximal peak and the average of the five highest peaks normalized to animal body weight were reported. Sera were obtained from Blood samples by retro-orbital puncture of anesthetized animals. All mice were received an intraperitoneal injection of Evans blue dye (EBD) (1 mg/g of body weight) 5 hours after the test. The mice were sacrificed 24 hours after EBD injection and the TA muscles were removed and quickly frozen in liquid nitrogen-cooled isopentane.

Serum Creatine Kinase Activity Measurement

The creatine kinase (CK) activity in serum was measured using VITROS CK Slides (Ortho-Clinical Diagnostics, Johnson & Johnson).

Western Blot Analysis

Protein samples were separated by SDS-PAGE electrophoresis (4 to 12% gradient, NuPAGE Novex Bis-Tris Gel 1.0 mm, Life Technologies) and transferred onto an Immobilon-P Transfer Membrane (Millipore). Fifty micrograms of human, dog or mouse of serum protein were loaded per line. A Rabbit polyclonal antibody (pAb) to Myomesin-3 (1:1000; 17692-1-AP: Proteintech) and a goat polyclonal antibody to human CK-M (N-13, 1/500, Santa Cruz) were used as primary antibodies followed by corresponding IRDye-800CW-conjugated antibodies (1:10,000) according to the manufacturer's instructions (Li-Cor Biosciences). Infrared fluorescence of the secondary antibodies was read on an Odyssey Imaging System (LI-COR Biosciences). The Precision Plus Protein Standards (Bio-Rad) were used as molecular weight markers. Band intensities were measured by the Odyssey application software (LI-COR Biosciences, 2.1 version).

Histology and Immunostaining

Cryosections (8 μm thickness) were prepared from frozen muscles. Transverse sections were processed for hematoxylin phloxine saffron (HPS) staining and α-sarcoglycan immunostaining.

For colorimetric immunodetection of α-sarcoglycan, unfixed transverse cryosections were rehydrated with PBS for 5 min and then incubated with $H_2O_2$ for 20 min at room temperature (RT) to inhibit endogenous peroxidases. After washing with PBS, sections were blocked with PBS/10% goat serum for 30 min and then incubated with 1/1000 dilution of a rabbit polyclonal primary antibody directed against amino acids 366-379 of the human α-sarcoglycan sequence (AC-ahSarco57) 1 to 2 h at RT. After washing with PBS, sections were incubated with secondary antibody conjugated with horseradish peroxidase (HRP) diluted 1/200 for 1 h at RT. Sections were washed 3 times with PBS and then incubated with diluted diaminobenzidine (DAB; DAKO) for 2-5 min. Then, sections were successively treated with ethanol (5 min), twice in xylene (5 min), mounted with Eukkit (Labonord, France) and visualized on a Nikon microscope.

Results

Dystrophin

Identification of Myomesin 3 Fragments in Sera of DMD Patients by Mass-Spectrometry Mass spectrometry (LC-MS/MS) analysis of 4 DMD patients and 6 healthy controls revealed the presence of myomesin 3 exclusively in the DMD samples. Peptides matching myomesin-3 were detected in 3 from 4 DMD patients (FIG. 10). Apart a gap of the first 300 amino acids, peptides were distributed all along the myomesin-3 protein (FIG. 10).

Myomesin 3 is a 162 kDa structural protein localised on the M line of the sarcomere in striated skeletal muscles. It belongs to the myomesin family further comprising myomesin 1 and myomesin 2 (M protein). These proteins are composed mainly of immunoglobulin-like and fibronectin domains (a unique N-terminal domain, two Ig domains (Ig2-3), 5 Fn domains (Fn4-8) and 5 C-terminal Ig domains (Ig9-13). It has been shown that they bind to myosin by their N-terminus and titin by their central part and that they dimerize by their C-terminus. A binding of the M protein and myomesin with creatine kinase has also been reported. Myomesin 3 is found in skeletal muscle and appears to be specifically expressed in the fibers of the intermediate type and to a lesser extent in the slow fibers. These proteins are involved in sarcomere structure allowing anchoring of myosin and titin to the line M. They also allow sarcomeres to withstand the mechanical stresses thanks to their elastic properties.

Presence of Myomesin 3 Fragments in the Serum of Patients with Duchenne Muscular Dystrophy Western blot analysis with antibodies against the C-terminal part of myomesin 3 showed the presence of two fragments of 110 kDa and 140 kDa in the sera of patients with Duchenne dystrophy (FIG. 1). These fragments were undetectable in all healthy subjects. Five patients with Duchenne muscular dystrophy have been analyzed so far.

Presence of MYOM3 Fragments in Sera of GRMD Dogs

Western blot analysis of sera from canine model of DMD (GRMD dog) revealed the presence of two bands migrating at the same positions as C-ter fragments of human MYOM3 (FIG. 2). A total of 40 dogs GRMD and 30 healthy controls aged from 40 days to 1 year and a half have been tested. These fragments were exclusively present in sera from all the affected animals.

Presence of MYOM3 Fragments in Sera of Mdx Mice

The presence of the MYOM3 fragments was analyzed on mice aged 1 week to 1 year by Western blot analysis. The fragments were detected in all mdx mice at all ages tested (from 1 day to 6 months: FIGS. 3, 4 and 10) and were absent in the healthy controls (a total of about 100 mdx and 100 control mice were tested). Interestingly, the level of MYOM3 in the sera increased progressively with mouse aging and did not correlate with the timing of the acute phase of muscle necrosis, which occurs generally at three to four weeks of age, followed by an apparent stabilisation of the mouse phenotype. The kinetic of creatine kinase level is quite different from those of MYOM3: firstly, there are substantial inter-individual variations in the CK level; secondly the high level of CK was already seen at the birth (1 day of age), but at one week age CK was undetectable, raising again at 2 week and further augmenting at 4 weeks age (FIGS. 3, 4). Importantly, the level of CK at birth can be higher in the healthy controls compared to mdx mice (FIG. 2).

Similarity in the MYOM3 fragment sizes between different species could imply similar mechanisms of myomesin-3 processing in this dystrophy.

Steady Level of the MYOM3 Fragments in the Serum of mdx Mice Subjected to Physical Exercise.

To follow the impacts of physical exercise on myomesin-3 and creatine kinase levels in sera, healthy and mdx mice were subjected to downhill running for 30 min. All 6 healthy mice were able to run during 30 min without signs of wearing. In contrast, only 1 mdx mouse was able to complete the exercise (mdx n° 1) while the others stopped after 10 min (2 mice) or 15 min (3 mice). The fragments of MYOM3 were present at all time-points in serum from mdx mice with only a slight increase of intensity at 24 h and 48 h, while the level of CK varied substantially being at least four times higher 3 hours post-exercise compared to the level before the exercise (FIG. 5). Importantly MYOM3 fragments were not detected in serum of healthy controls while creatine kinase was detected at different levels in serum of all healthy mice without noticeable correlation with physical exercise. In conclusion, the analysis of the impact of exercise (treadmill running) on the presence of myomesin-3 fragments in the serum of mdx mice showed no increase in these fragments after exercise unlike the increase in creatine kinase.

Alpha-Sarcoglycan

The Fragments of Myomesin 3 are Present in the Sera of LGMD2D Patients.

In order to know whether the presence of MYOM3 in serum is a specific feature of DMD patients or this protein can be also detected in serum from patients with other dystrophic muscle diseases, we analyzed serum from 3 available LGMD2D patients. Western blot analysis demonstrated that MYOM3 fragments of the same size as in DMD patients were present in the sera of all of the three patients (FIG. 6), while no fragments were seen in the healthy controls.

Stable Presence of Fragments in the Serum of KO-Sgca Mice Subjected to Physical Exercise (Alpha-Sarcoglycanopathy Model).

The presence of these fragments was analyzed by Western blot at rest and at different time points after muscular effort (escape test) (FIG. 7). The level of MYOM3 fragments after exercise stayed at the same level as at rest.

The Level of Myomesisn-3 Fragments in Sera Correlates with the Efficiency of Gene Transfer and Mouse Muscle Strength.

We then analyzed the level of myomesin-3 fragments in sera after gene therapy of the KO-Sgca mice. To this goal KO-Sgca mice received intravenous injection with two different doses (1e11 and 5e11 viral genomes (vg)) of AAV8 coding for human alpha-sarcoglycan (SGCA) under the control of desmin promoter. The efficiency of the therapy was evaluated by immunostaining of Sgca and by hematoxylin phloxine saffron (HPS) stain on muscle sections 56 days after rAAV8 injections (FIG. 8). At the low vector dose about 10% of the fibers expressed SGCA, while at the highest dose 90% of the fibers were SGCA-positive. The HPS stain confirmed the improvement of muscle morphology with the increase of the vector doses. Importantly, the level of MYOM3 fragments in sera of KO Sgca mice decreased with the increase in the efficiency of gene transfer. This effect was already visible 14 days after AAV injection and persisted after 56 days post-injection. Correlation analysis between the mouse muscle force measured by Escape Test and the level of serum MYOM3 fragments demonstrated a tight correlation between these values ($r2=0.7616$). No statistically significant correlation was found between muscle force after gene therapy and serum CK level ($r2=0.2619$) (FIG. 8).

Other Diseases

Presence of Myomesin 3 Fragments in Serum From Mouse Models of Other Dystrophies.

Analysis of MYOM3 was performed by Western blot in sera from mice models for different dystrophies (KO-Sgca, MDX, KO-Dysf, KO-Capn3 and KO-Sgcg) and controls (C57B16) (see Table 1 for the description of models) at the age of 4 weeks and 6 months. The high level of MYOM3 fragments were found at the both ages in MDX, KO-Sgca and KO-Sgcg mice while in KO-Dysf these fragments were barely detectable at 1 month age and reached its maximum at the age of 6 month. Only a faint labelling of MYOM3 fragment was detected in KO-Capn3 mice (FIG. 9). Interestingly, among the studied murine models of muscular dystrophies, KO-Capn3 demonstrated the weakest phenotype suggesting that the myomesin 3 serum level could correlate with the severity of the disease. In order to reinforce this hypothesis, we evaluated the level of the myomesin-3 fragments in KI-FKRP mice, a mouse model for LGMD-21. Contrary to the disease in human, mutation of the Fukutin-related protein gene in mice leads to a very mild phenotype with no myomesin 3 fragments in the serum thus confirming correlation between the severity of the dystrophy with the level of myomesin-3 fragments in serum.

Example 2

In the present example, the inventors have completed their study, and show in particular that myomesin proteins are relevant tools to determine whether or not a patient carries muscular dystrophy, prediction of the development of muscular dystrophy, screening for a therapeutic agent or technique for muscular dystrophy, or for the evaluation of the efficacy of a therapeutic agent or technique for muscular dystrophy.

Materials and Methods

Human Sample Collection

The human studies were conducted according to the principles of the declaration of Helsinki "Ethical Principles for Medical Research Involving Human Subjects". Serum samples from a cohort of 39 young (3 to 10 years old) and 17 older (12 to 20 years old) DMD patients as well as 29 young (3 to 10 years old) and 18 older (12 to 20 years old) healthy individuals were collected at the Cincinnati Children's Hospital Medical Center USA (US cohort) as part of ADNA (Avancées Diagnostiques pour de Nouvelles Approches thérapeutiques) project (see Worldwide Website: institut-merieux.com/projetssante_adna.php). The study protocol and Informed Consent was approved by the Institutional Review Board (IRB) at Cincinnati Children's Hospital Medical Center. Informed Consent was obtained from all subjects prior to the study. The conduct of the study conforms to all applicable human subjects research regulations. Serum samples from 3 LGMD2D patients were collected at the Neuromuscular Research Center (University Hospital of Tampere, Finland) during standard day-care consultation. After collection, samples were centrifuged twice immediately (10,000×g, 10 min) and serum was stored at −80° C.

Protein Quantification and Measurements of Creatine Kinase Activity

Protein concentration was determined using the Bio-Rad Protein Assay Dye Reagent (Bio-Rad) according to the manufacturer's instructions with bovine serum albumin as a standard. Measurements of total creatine kinase (CK) activity were performed using the Vitros DT60 II Chemistry System according to the manufacturer's instructions (Ortho-Clinical Diagnostics).

Serum Depletion

Depletion of the 12 most abundant serum proteins (alpha 1-acid glycoprotein, alpha 1-antitrypsin, alpha 2-macroglobulin, albumin, apolipoprotein A-I, apolipoprotein A-II, fibrinogen, haptoglobin, IgA, IgG, IgM and transferrin) was performed with the Proteome purify 12 Human Serum Protein Immunodepletion kit (R&D Systems) according to the manufacturer's instructions with some modifications. Briefly, 1 ml of immunodepletion resin was mixed with 10 µl of pooled serum diluted with PBS to a final volume of 500 µl and incubated for 1 h at room temperature (RT). Depleted serum was collected after centrifugation (1000× g, 2 min) in Spin-X Filter Units and proteins were 5-fold concentrated using Amicon Ultra-2 Centrifugal Filter Units (cut-off 3000 kDa; Millipore) following the manufacturer's instructions.

Mass Spectrometry

For mass spectrometry analysis, 10 µg of depleted serum proteins were solubilised in a total of 123 µl of the reaction mixture containing 4 M urea, 1.5 M thiourea and 50 mM tris-HCl pH 8.3. Proteins were reduced with 10 mM dithiothreitol for 30 min and then alkylated with 55 mM iodoacetamide for 20 min. Alkylated proteins were first digested with 500 ng of endopeptidase lys-C (Wako) for 3 h at RT. Then, the mixture was adjusted to 235 µl with MilliQ-water and treated with 500 ng of trypsin (Sequence Grade Trypsin, Promega) for 16 h at RT. Enzymatic activity was stopped by addition of formic acid to 3% final concentration and samples were stored at −20° C. until use. The peptide mixture was desalted using ZipTip$_{\mu-C18}$ Pipette Tip (Millipore) and separated with an Easy nano-LC Proxeon system (Thermo Fisher Scientific) equipped with a reversed phase C18 column (Easy-Column Proxeon C18, L 10 cm, ID 75 µm). Eluates were monitored by a LTQ Velos Orbitrap mass spectrometer (Thermo Fisher Scientific) and tandem MS (MS/MS) data were processed with Proteome Discoverer 1.4 software (Thermo Fisher scientific) coupled to an in house Mascot search server (Matrix Science, 2.3.2 213 version) using SwissProt database as described previously (Rouillon et al., 2014). The relative abundance of each protein identified in serum from DMD or healthy patients was estimated by label-free quantification using the Progenesis LC-MS software (Nonlinear Dynamics, 4.0 version).

Western Blot

Protein samples were separated by SDS-PAGE electrophoresis (4 to 12% gradient, NuPAGE Novex Bis-Tris Gel 1.0 mm, Life Technologies) and transferred onto Protran Premium membrane (nitrocellulose, GE Healthcare). Fifty micrograms (1 µl of serum) of human, mouse, or dog serum protein were loaded per lane. Antibodies against MYOM3 (1:1000, Proteintech: 17692-1-AP) and the CK-M (1:500, Santa Cruz: sc-15161) were used as primary antibodies followed by incubation with the corresponding IRDye-800CW-conjugated antibodies (1:10,000, LI-COR Biosciences) according to the manufacturer's instructions. Infrared fluorescence of the secondary antibodies was read on an Odyssey Imaging System (LI-COR Biosciences). Band intensities were measured by the Odyssey application software (LI-COR Biosciences, Image Studio Lite 4.0 Version).

Animal Experimentations

Animal experimentations were conducted in accordance with the European guidelines for the protection of vertebrate animals used for experimental purposes (Directive 2010/63/EU of 22 Sep. 2010) and for the mice treated with the oligonucleotide Pip6a-PMO, in accordance to procedures authorised by the UK home office. Blood samples were collected from male dogs (provided by the CEDS at Mézilles and Oniris at Nantes, France) from the lateral saphenous vein and from mice by retro-orbital bleeding or from the jugular vein. The following mouse strains were used: C57BL/6 and C57/BL10 control strains as well as mdx (model for DMD; Chapman, 1989), and 4 knockout (KO) strains named KO-Capn3 (model for LGMD2A; Laure, et al., 2009), KO-Dysf (model for LGMD2B; Lostal, et al., 2010), KO-Sgcg (model for LGMD2C; Hack, et al., 1998) and KO-Sgca (model for LGMD2D; Duclos, et al., 1998). Blood samples were centrifuged twice (10,000× g, 10 min, 4° C.) and serum samples obtained were stored at −80° C. until use.

Physical Exercise of Mice

Mice were placed on a treadmill (Treadmill Exer 6M, Columbus Instruments) to run at a downward inclination of 15° at speeds of 8 m/min for 5 min, followed by 12 m/min for 25 min. Serum samples were collected by retro-orbital bleeding and stored at −80° C.

Ageing in Mice

Blood samples from 1-day up to 52-week-old mice (5 healthy controls or 5 mdx per age) were collected and stored at −80° C. Newborn as well as 12-, 24-, 36- and 52-week-old mice were euthanized after collection. The samples for the 1, 2, 3 and 4 week time points were collected from the same group of mice.

Antisense Oligonucleotide-Mediated Exon Skipping Therapy of mdx Mice

Twelve-week-old mdx mice were treated with a single 12.5 mg/kg tail vein injection of an arginine-rich cell-penetrating peptide conjugated to a phosphorodiamidate morpholino oligonucleotide, Pip6a-PMO (peptide RXRR-BRRXRYQMRXRBRXRB coupled through an amide linkage at the 3' of the oligonucleotide 5'-GGC-CAAACCTCGGCTTACCTGAAAT-3')(SEQ ID NO: 25), synthesised and prepared in a sterile saline solution as described previously (Betts et al, 2012; Roberts et al, 2012). Blood samples were collected prior and 2, 4 and 8 weeks post-injection and the serum levels of the MYOM3 fragments and CK-M were monitored by Western blot analysis.

Gene Therapy Treatment of KO-Sgca Mice

Recombinant adeno-associated virus 8 (rAAV2/8) vector was used to restore α-sarcoglycan expression in KO-Sgca mice. The production of rAAV was performed by dual infection of Sf9 cells with baculoviruses harbouring cDNA for Sgca under the desmin promoter and regulated by miR-142-3p (Boisgerault et al, 2013) and AAV rep2/cap8 genes (rAAV2/8). The purification was performed on immuno-affinity AVB SEPHAROSE medium (GE Healthcare) according to (Smith et al, 2009). Four groups of 5 week old KO-Sgca mice (5 mice per group, except 4 mice for the highest vector dose) were injected either with PBS or with increasing doses of rAAV (1e11, 5e11, and 1e12 viral genome (vg)). Blood samples were collected biweekly for 3 months and levels of the MYOM3 fragments and CK were monitored by Western blot analysis and measurements of CK activity, respectively. Muscle force was measured by the escape test 1 week before sacrifice. Restoration of the sarcoglycan complex and muscle morphology were assessed by immunostaining and histological analyses.

Evaluation of Muscle Force in Mice

Mouse muscle force was evaluated by the whole body tension method or escape test (Carlson & Makiejus, 1990) with some modifications. Mice attached to the tail with a thread connected to a tension transducer were placed on a platform facing the entrance of a 30 cm long tube. In response to pinching of the tail, mice try to escape within the tube thus raising a short peak of force (forward pulling tension, FPT) that is recorded. Five FPTs were recorded for each mouse. The body weight of each mouse was measured and the WBT was obtained by dividing the average of the 5 FPTs with the body weight.

Statistical Analysis

Statistical analyses were performed using the GraphPad Prism version 6.04. Data are expressed as mean±SD if not otherwise specified. For comparisons between means, homogeneity of variances was assessed by Fisher-Snedecor's test and the Student's t-test (two-tailed) was applied. Pearson's correlation was used for correlation studies and data were analyzed with a 95% confidence interval and P<0.05 was considered significant.

Histology and Sgca Immunostaining

Cryosections (8 mm thickness) were prepared from frozen right and left gastrocnemius muscles. Transverse sections were processed for hematoxylin phloxine saffron (HPS) histological staining. Colorimetric immunodetection of Sgca was performed as previously described (Fougerousse et al, 2007).

After digitization of immunostained biopsies (Axioscan, ZEISS) the total surface of the biopsies and the surface stained for α-sarcoglycan were quantified using the ImageJ software (version 1.47g 64-hits, Rasband, W.S., ImageJ, U.S. National Institutes of Health, Bethesda, Md., USA, see Worldwide Website: imagej.nih.gov/ij/, 1997-2014) and a customized script (available on demand). The percentage of Sgca positive fibres for a given biopsy was calculated using the following equation: (number of Sgca positive pixels on the biopsy area/surface in $\mu m^2$ of the biopsy area) divided by the same ratio obtained for healthy control (number of Sgca positive pixels on the biopsy area/surface in $\mu m^2$ of the biopsy of the control C57BL/6J mouse) and multiplied by 100.

Results

Detection of Differentially Expressed Serum Proteins in DMD Patients by Mass Spectrometry Serum samples from 39 patients and 38 control subjects collected in USA as part of the ADNA project (see Worldwide Website: institut-merieux.com/projetssante_adna.php) (the entire US cohort comprised 103 patients and control subjects) were analysed using a mass spectrometry approach. To reduce the number of LC-MS/MS analyses, the samples were organised into 4 groups (G1: young DMD from 3 to 10 years old; G2: older DMD from 12 to 20 years old; G3: young controls from 3 to 10 years old; and G4: older controls from 12 to 20 years old) subdivided in a total of 12 pools according to the patient's age (Table 2). Each pool included sera from at least 4 individuals where serum of each individual was equally represented. In order to ensure deep proteome coverage, the pools were immunodepleted for the 12 major serum proteins.

TABLE 2

List of differentially expressed proteins between G1 and G3 groups (young DMD and age matched healthy controls) classified by the decrease in the ratio DMD/healthy (fold change). Top 10 proteins with the lowest p-value are in bold. All shown proteins passed thresholds of peptide numbers ≥2, a score ≥50, a fold change ≥2 and a p-value ≤0.05. Peptides: number of peptides identified for a given protein. Score: Mascot protein score.

| No. accession | Description | Localization | Peptides | Score | ANOVA (p-value) | Fold change |
|---|---|---|---|---|---|---|
| MYG_HUMAN | Myoglobin | Cytoplasm | 4 | 195 | 2.7e−03 | 234.8 |
| MYOM2_HUMAN | MYOM2 | Myofibril | 10 | 390 | 9.8e−05 | 100.1 |
| MYOM3_HUMAN | MYOM3 | Myofibril | 11 | 491 | 1.5e−05 | 49.7 |
| TPIS_HUMAN | Triosephosphate isomerase | Cytoplasm | 3 | 128 | 2.3e−03 | 48.4 |
| AATC_HUMAN | Aspartate aminotransferase | Cytoplasm | 3 | 75 | 4.7e−04 | 45.7 |
| KCRM_HUMAN | CK-M | Cytoplasm | 15 | 849 | 2.9e−05 | 39.8 |
| MYH7_HUMAN | Myosin-7 | Myofibril | 11 | 520 | 2.2e−05 | 38.3 |
| ENOB_HUMAN | β-enolase | Cytoplasm | 4 | 178 | 7.4e−05 | 34.8 |
| G6PI_HUMAN | Glucose-6-phosphate isomerase | Cytoplasm/Secreted | 4 | 130 | 1.6e−03 | 29.5 |
| CAH3_HUMAN | Carbonic anhydrase 3 | Cytoplasm | 5 | 182 | 8.6e−05 | 23.9 |
| FLNC_HUMAN | Filamin-C | Myofibril | 4 | 145 | 4.3e−04 | 19.4 |
| ALAT1_HUMAN | Alanine aminotransferase 1 | Cytoplasm | 4 | 127 | 3.0e−05 | 15.6 |
| ALDOA_HUMAN | Fructose-bisphosphate aldolase A | Cytoplasm | 15 | 729 | 9.3e−05 | 14.2 |
| KPYM_HUMAN | Pyruvate kinase PKM | Cytoplasm | 16 | 845 | 1.1e−05 | 12.8 |
| TITIN_HUMAN | Titin | Myofibril | 14 | 495 | 1.9e−03 | 10.8 |
| VINC_HUMAN | Vinculin | Cytoplasm/Membrane | 2 | 74 | 7.2e−05 | 10.3 |
| PYGM_HUMAN | Glycogen phosphorylase, muscle form | Cytoplasm | 8 | 257 | 6.1e−04 | 9.9 |
| LDHA_HUMAN | L-lactate dehydrogenase A chain | Cytoplasm | 8 | 378 | 9.1e−04 | 9.5 |
| HPT_HUMAN | Haptoglobin | Secreted | 29 | 1867 | 1.5e−04 | 7.6 |
| HBD_HUMAN | Hemoglobin subunit δ | Cytoplasm | 3 | 100 | 5.1e−03 | 6.2 |
| LDHB_HUMAN | L-lactate dehydrogenase B | Cytoplasm | 10 | 598 | 2.4e−05 | 5.4 |
| HBB_HUMAN | Hemoglobin subunit β | Cytoplasm | 7 | 552 | 8.0e−03 | 3.6 |
| HBA_HUMAN | Hemoglobin subunit α | Cytoplasm | 7 | 407 | 5.3e−03 | 3.4 |
| TPM2_HUMAN | Tropomyosin βchain | Myofibril | 5 | 170 | 2.0e−02 | 2.6 |
| VASN_HUMAN | Vasorin | Membrane | 4 | 135 | 4.0e−02 | 0.5 |
| ALS_HUMAN | Insulin-like growth factor-binding protein complex | Secreted | 22 | 1096 | 1.0e−02 | 0.5 |
| PHLD_HUMAN | Phosphatidylinositol-glycan-specific phospholipase D | Secreted | 9 | 533 | 4.7e−03 | 0.5 |
| CHL1_HUMAN | Neural cell adhesion molecule L1-like protein | Membrane/Secreted | 2 | 66 | 3.0e−02 | 0.5 |

TABLE 2-continued

List of differentially expressed proteins between G1 and G3 groups (young DMD and age matched healthy controls) classified by the decrease in the ratio DMD/healthy (fold change). Top 10 proteins with the lowest p-value are in bold. All shown proteins passed thresholds of peptide numbers ≥2, a score ≥50, a fold change ≥2 and a p-value ≤0.05. Peptides: number of peptides identified for a given protein. Score: Mascot protein score.

| No. accession | Description | Localization | Peptides | Score | ANOVA (p-value) | Fold change |
|---|---|---|---|---|---|---|
| COL11_HUMAN | Collectin-11 | Secreted | 2 | 72 | 2.6e−03 | 0.4 |
| CADH5_HUMAN | Cadherin-5 | Membrane | 6 | 220 | 2.0e−03 | 0.4 |
| CD109_HUMAN | CD109 antigen | Membrane | 2 | 59 | 3.0e−02 | 0.4 |
| LBP_HUMAN | Lipopolysaccharide-binding protein | Secreted | 7 | 386 | 5.0e−03 | 0.4 |
| CRAC1_HUMAN | Cartilage acidic protein 1 | Secreted | 6 | 223 | 2.0e−02 | 0.4 |
| C4BPB_HUMAN | C4b-binding protein | Secreted | 4 | 207 | 2.0e−02 | 0.4 |
| CNDP1_HUMAN | β-Ala-His dipeptidase | Secreted | 8 | 294 | 4.2e−03 | 0.3 |
| DPP4_HUMAN | Dipeptidyl peptidase 4 | Membrane/Secreted | 5 | 162 | 5.5e−03 | 0.3 |
| CETP_HUMAN | Cholesteryl ester transfer protein | Secreted | 7 | 296 | 8.2e−04 | 0.2 |

Mass spectrometry analysis of serum samples of all 12 subgroups enabled the identification a total of 3329 unique peptides matching 378 proteins (with a false discovery rate less than 0.01). Among those, 69% of protein identification calls (260 proteins) were based on spectra from 2 or more peptides. To reveal proteins differentially present in sera from DMD and healthy individuals, the data were analysed by a label-free quantification approach using the following parameters: number of peptides ≥2; protein score ≥50 and fold change ≥2. The analysis of G1 versus G3 groups revealed 24 proteins more abundant in DMD and 13 in healthy subjects (Table 3). The top 10 proteins with the lowest p-value were overexpressed in DMD patients and either involved in muscle energy metabolism (pyruvate kinase PKM, L-lactate dehydrogenase B chain, CK-M, alanine aminotransferase 1, β-enolase, carbonic anhydrase 3, fructose-bisphosphate aldolase A), in sarcomere organisation (myomesin-3, myosin-7) or costamere organisation (vinculin).

bisphosphate aldolase A, L-lactate dehydrogenase B chain, and hemoglobin β) and 4 in healthy subjects (gelsolin, phosphatidylcholine-sterol acyltransferase, cadherin-13, cartilage acidic protein 1) (Table 3). Only 4 of these proteins (CK-M, fructose-bisphosphate aldolase A, L-lactate dehydrogenase B chain and hemoglobin β) were differentially abundant in both DMD age groups according to the mass spectrometry analysis. Importantly, the expression ratios for these four proteins in DMD versus healthy controls were substantially lower in older DMD patients as compared to the young DMD group (19.5; 3.3; 2.2 and 2.4 folds in older DMD versus 39.8; 14.2; 5.4 and 3.6 times in young, respectively). The decrease in the number of differentially expressed proteins and in magnitude of their fold changes is most probably due to the drastic decrease of muscle mass in older DMD patients (12-20 years old), and relative immobility of these patients. Interestingly, label-free analysis of young and older DMD patients (G1 versus G2) revealed 8 secreted proteins that increased in abundance with patient age (dopamine β-hydroxylase: 3 fold, adiponectin: 3 fold,

TABLE 3

List of differentially expressed proteins in serum samples between G2 and G4 groups (older DMD and age matched healthy controls) classified by the decrease in the ratio DMD/healthy (fold change). All shown proteins passed thresholds of peptide numbers ≥2, a score ≥50, a fold change ≥2 and a p-value ≤0.05. Peptides: number of peptides identified for a given protein. Score: Mascot protein score.

| No. accession | Description | Localization | peptides | Score | ANOVA (p-value) | Fold change |
|---|---|---|---|---|---|---|
| KCRM_HUMAN | CK-M | Cytoplasm | 3 | 96 | 1.0e−02 | 19.5 |
| ADIPO_HUMAN | Adiponectin | Secreted | 3 | 213 | 3.0e−02 | 4.4 |
| ALDOA_HUMAN | Fructose-bisphosphate aldolase A | Cytoplasm | 2 | 84 | 3.0e−02 | 3.3 |
| HBB_HUMAN | Hemoglobin subunit β | Cytoplasm | 9 | 632 | 8.4e−03 | 2.4 |
| LDHB_HUMAN | L-lactate dehydrogenase B chain | Cytoplasm | 6 | 223 | 4.0e−02 | 2.2 |
| GELS_HUMAN | Gelsolin | Cytoplasm | 32 | 2287 | 1.0e−02 | 0.5 |
| LCAT_HUMAN | Phosphatidylcholine-sterol acyltransferase | Secreted | 6 | 295 | 1.0e−02 | 0.4 |
| CAD13_HUMAN | Cadherin-13 | Membrane | 2 | 86 | 5.8e−03 | 0.4 |
| CRAC1_HUMAN | Cartilage acidic protein 1 | Secreted | 3 | 105 | 1.0e−02 | 0.2 |

Comparison of older DMD patients with their age matched controls (G2 versus G4) using the same parameters resulted in only 9 differentially expressed proteins: 5 proteins more abundant in DMD (CK-M, adiponectin, fructose-bisphosphate aldolase A, L-lactate dehydrogenase B chain, hemoglobin β) and 4 in healthy subjects (gelsolin, serum amyloid P-component: 3 fold, insulin-like growth factor-binding protein complex acid labile subunit: 3 fold, β-Ala-His dipeptidase: 5 fold, insulin-like growth factor I: 5 fold).

Levels of MYOM3 Demonstrate Less Inter-Individual Variations Compared to CK in DMD Patients Elevated levels of cytosolic myofibrillar proteins such as CK in the blood are now widely used as the first stage of DMD diagnosis (Gasper & Gilchrist, 2005; Moat et al, 2013). Therefore, it was appealing to compare serum levels of CK with one of the myofibrillar structural proteins found in the present study. Based on the high fold change (50) and low p-value (1.5e-5) between DMD and healthy controls (Table 2), MYOM3 protein (UniProtKB #Q5VTT5) was chosen for further analysis. MYOM3, a protein of 1437 amino acids (162.2 kDa), is a member of a family of closely related structural proteins detected at the M-band of the sarcomere in striated skeletal muscles: MYOM1, MYOM2 (or M protein) and MYOM3. These proteins are involved in sarcomere stability and resistance during intense or sustained stretching (Schoenauer et al., 2008). Detailed analysis of MS/MS data showed that the 25 identified peptides were equally distributed along the MYOM3 sequence indicating that the entire protein (or fragments covering the entire length of the protein) was present in serum.

As mentioned in example 1, western blot analysis of serum from DMD patients with an anti-MYOM3 antibody targeting the last 325 amino acids at the C-terminus revealed the presence of two bands of 100 and 140 kDa respectively (FIG. 11). Given that intact MYOM3 has a predicted size of 162 kDa, this suggests that these two bands correspond to C-terminal fragments of the protein. Importantly, fragments of the same size were barely detectable in sera from healthy subjects, thus validating the mass spectrometry data.

We next compared the levels of the MYOM3 fragments and CK in all 103 subjects from the US cohort. The serum expression levels of both MYOM3 fragments were determined by Western blot analysis and CK assessed by measuring its enzymatic activity (FIG. 12). In accordance with the mass spectrometry data, results showed that expression levels of both, CK and the MYOM3 fragments, were much higher in young DMD patients compared to the respective healthy controls (ratio DMD/Control: CK=193 and MYOM3=185) (FIGS. 12A and 12B). In older DMD patients, the expression levels of CK and MYOM3 fragments were respectively 14 and 5 times lower than in young DMD patients.

Importantly, even if both proteins were able to discriminate DMD patients and healthy controls, there were less inter-individual variations in MYOM3 fragment levels compared to CK levels. While the CK levels in the young patients varied from 9000 IU/L to 60 000 IU/L (mean 27130 IU/L±13130), the values for MYOM3 fragments remained between 11 a.u. and 24 a.u. (mean 19 a.u.±3). The low correlation observed between the levels of serum CK and MYOM3 fragments in the group of young patients ($R^2=0.28$) indicates that different physiological mechanisms may account for the secretion/stability of these proteins at this age. (FIG. 12C). Conversely, these two biomarkers were well correlated in older patients (FIG. 12D).

MYOM3 Fragments are Specifically Present in Sera from Animal Models of DMD.

The levels of MYOM3 fragments were quantified in two animal models of DMD: Golden Retriever muscular dystrophy (GRMD) which has a severe phenotype similar to DMD patients (Kornegay et al, 2012) and dystrophin-deficient mdx mice. Western blot analysis of GRMD and mdx sera revealed the presence of 2 bands migrating at the same positions as human MYOM3 fragments. Importantly, the abundance of these fragments was 100 times higher than in the healthy control dogs (FIGS. 13A, B). Whereas the level of the MYOM3 fragments in human DMD samples decreased with age, expression of these fragments was very similar in the serum of 2 and 18 month old GRMD (GRMD dogs usually do not survive beyond this age without special care). Age-independent expression of the MYOM3 fragments could be an advantage for utilisation of this biomarker in gene therapy studies conducted in dogs.

MYOM3 Fragments are Specifically Expressed in Sera of LGMD2D Patients and Mouse Models of LGMDs.

The presence of the MYOM3 fragments was also analysed in serum samples of 3 patients with α-sarcoglycanopathy (LGMD2D). Fragments of the same length (100 and 140 kDa) were detected at elevated levels in all these patients. Overall, the level of these fragments in LGMD2D patients was lower compared to their intensity in young DMD patients (FIG. 14A). The following mouse models of limb girdle muscular dystrophies were included in this study: KO-Calpain 3 (models for LGMD2A) (Richard et al, 2000), KO-Dysferlin (models for LGMD2B) (Lostal et al, 2010), KO-Sgcg (models for LGMD2C) (Hack et al, 1998), and KO-Sgca (models for LGMD2D) (Duclos et al, 1998). These mouse models are congenic strains on the genetic background of the C57BL/6J mouse, which was included in the study as their wild type (WT) control. Taking into consideration the muscle impairment and time of disease onset, these mouse models can be classified in terms of decreasing order of severity: KO-Sgca, KO-Sgcg, KO-dysf and KO-Capn3. Serum from these mouse models was collected at 1 and 6 months of age, corresponding to the early and advanced stages of the dystrophies, and the levels of the MYOM3 fragments were compared by Western blot. The highest levels of serum MYOM3 fragments were observed in the three mouse models with perturbations in the DAPC (FIG. 14B). In KO-Dysf mice, these fragments were barely detectable at 1 month of age and then increased at 6 months, reflecting the aggravation of the disease at this age. MYOM3 fragments were hardly detectable in KO-Capn3 mice at any age.

In Mdx Mice, the MYOM3 Fragments are Expressed Early, Demonstrate Less Inter-Individual Variability and are Less Sensitive to Physical Exercise Compared to CK.

In order to identify the earliest time point when the serum MYOM3 fragments are detectable, we investigated sera from mdx mice of different ages (from birth to 1 year old). The MYOM3 fragments were detected in mdx mice at birth, with a small decrease in their levels at 1 week of age and followed by a rise in abundance at 3 weeks (FIG. 15A). Importantly, the levels of these fragments in the age-matched control mice was lower at all ages tested (FIG. 15B). The kinetics of the MYOM3 fragment abundance in the serum of mdx mice correlates with the timing of an acute phase of muscle necrosis generally occurring at 3 to 4 weeks of age, followed by an apparent stabilisation of the muscle phenotype (Cullen & Jaros, 1988). The kinetics of serum CK levels in mdx mice were different from that of the MYOM3 fragments during the first weeks of age. Consistent with previous studies (McArdle et al, 1994; Wooddell et al, 2010) serum CK was elevated in newborn mice, but then became undetectable during the 1st and 2nd week of age (except for 1 mouse), rising again at 3 and 12 weeks followed by a stabilisation (FIG. 15C). In healthy mice serum CK was also slightly elevated in newborns and 12- and 24-week-old animals (FIG. 15D). Importantly, less variation was observed in the levels of MYOM3 fragments in mice of the same age compared to the CK (maximum fold change 2 for MYOM3 versus 110 for CK). The difference in age-dependent expression patterns between serum CK and MYOM3 fragments in mdx mice is probably related to different mechanisms of bioprocessing of these proteins, especially during the early phases of disease.

To assess the impact of physical exercise on the serum levels of the MYOM3 fragments and CK, WT and mdx mice were subjected to downhill running for 30 min. This exercise regimen is often used to increase muscle injury and worsen the mdx phenotype (Brussee et al, 1997; Vilquin et al, 1998). Sera were collected 7 days before and 3, 24 and 48 hours after exercise. Importantly, while in mdx mice CK concentration peaked at 3 hours post-exercise (up to 10 fold increase) followed by a substantial decrease (FIG. 16C), physical exercise had relatively little impact on the serum levels of the MYOM3 fragments (less than 2 fold increase 48 h post-exercise) (FIG. 16A). Interestingly, in healthy mice, there was a slight increase in the levels of the MYOM3 fragments 24 and 48 h after exercise, even though the maximum level of the fragments in healthy mice was 50 fold less than in mdx mice (FIG. 16B). Serum CK levels were variable in healthy mice without noticeable correlation with physical exercise (FIG. 16D). Given that MYOM3 is predominantly expressed in slow and intermediate speed (type I and IIa) skeletal fibres (Schoenauer et al, 2008) which are less affected in DMD relative to fast myofibres (Webster et al, 1988), it is possible that the difference in the kinetics of these biomarkers is partially due to the differential sensitivity of these muscle fibre types to exercise-induced damage.

MYOM3 Fragments Enable Monitoring of Pharmaco- and Gene Therapy Treatment Efficacy.

The presence of the MYOM3 fragments in serum of DMD and LGMD2D patients and their respective mouse models prompted us to evaluate the utility of these biomarkers for monitoring the response to experimental therapies in mdx and KO-Sgca mice.

Restoration of dystrophin expression in mdx mouse muscles was achieved by a single administration of an arginine-rich cell-penetrating peptide (CPP) conjugated to a phosphorodiamidate morpholino oligonucleotide (PMO) that efficiently induces skipping of exon 23 and restores dystrophin protein expression and muscle function (Betts et al, 2012; Yin et al, 2011). In order to evaluate the impact of the restoration of dystrophin expression on the serum levels of MYOM3 fragments and CK, blood samples from treated mdx, non-treated mdx and WT control mice were collected 2, 4 and 8 weeks post-injection. Two weeks after injection, the levels of the MYOM3 fragments in treated mdx mice substantially decreased (without reaching the level in the control mice) and then gradually increased over time (FIG. 7A). These data are in a good agreement with the restoration of the dystrophin expression observed in 30 to 60% of muscle fibres 2 weeks after injections (Betts et al, 2012; Yin et al, 2011), followed by a decrease in the percentage of positive fibres at later time points (Jearawiriyapaisarn et al, 2010). In contrast to the MYOM3 fragments, CK levels did not reflect restoration of dystrophin expression. Thus, 2 weeks after injection the level of serum CK was lower in treated mdx mice compared to WT control mice (FIG. 17B), while dystrophin expression did not exceed 60% at that time. Moreover, 8 weeks after the treatment, when the estimated level of dystrophin-positive fibres was around 20% (Betts et al, 2012; Yin et al, 2011), CK levels were higher in treated than in non-treated mdx mice. Different behaviour of the MYOM3 fragments and CK after partial restoration of dystrophin expression may reflect the capacity of these biomarkers to differentially reveal intracellular process such as microparticle turnover (Duguez et al, 2013) or increased myofibrillar protein catabolism (McKeran et al, 1977; Mussini et al, 1984).

To restore α-sarcoglycan expression in KO-Sgca mice, we used recombinant adeno-associated virus rAAV2/8 vector. Control C57BL/6J mice received an intravenous injection of PBS and four groups of KO-Sgca mice received intravenous injections of either PBS or low (1e11 vg), medium (5e11 vg) or high (1e12 vg) doses of rAAV2/8 coding for hSGCA. Mice were monitored for three months after the treatment. The following assays were compared in order to define the most appropriate for the follow up of the treatment: histological analysis of muscle biopsies (HPS staining and restoration of the sarcoglycan complex); total physical force 3 months after the treatment (1 week before animal sacrifice); biweekly analysis of serum CK and MYOM3 fragments levels.

Histological analysis of the gastrocnemius muscles demonstrated restoration of the complex in 5-30% (mean 15.6±8.4), 60-100% (mean 79.2±16.7), and 84-100% (mean 94.6±8.8) of fibres after low, medium and high rAAV dose treatments, respectively (FIGS. 18A, B). Importantly, by assessing the expression level of α-sarcoglycan (determined by immunostaining) the KO-Sgca, low, medium and WT mice could be clearly distinguished. However, no statistically significant difference was found between medium and high rAAV doses by this method. Importantly, this analysis is highly laborious, and the size of the biopsies makes it unsuitable for the follow-up of the therapeutic effect in small animals.

Similar to histological analysis, the conventional whole body tension method (WBT) is an end-point assay because mice become accustomed to the protocol (Carlson et al, 2010). The WBT method was only able to discriminate 2 clusters of animals: (1) KO-Sgca mice injected with PBS or low dose of rAAV and (2) control C57BL/6J mice and KO-Sgca mice injected with medium or high doses of rAAV (FIG. 18C).

A threshold 3000 IU/L of CK clearly separates KO-Sgca mice injected with PBS from all other experimental groups (FIGS. 18D, F). Nevertheless, when applying the Student's test (P-value threshold <0.01), differences only between few time points/injection doses appeared as statistically significant (FIG. 18F). Changing of the p-value threshold to <0.05 permits to distinguish more experimental groups of mice (FIG. 18F). Lower CK levels in all groups of mice at day 90 (one week after the total force measurements) (FIG. 18D) could be explained by the fact that an increase of CK levels after physical exertion is followed by a substantial decrease persisting for 2 weeks (Kobayashi et al, 2012).

Inter-individual variations of the MYOM3 fragment levels were lower compared to serum CK in the case of all experimental groups (FIGS. 18D, E). In accordance with a previous study showing progressive development of muscular dystrophy in KO-Sgca mice (Duclos et al, 1998) the levels of the MYOM3 fragments in the control mice injected with PBS increased gradually with age (FIG. 18E). Even the lowest dose of rAAV (1e11 vg) stabilised the MYOM3 fragment levels, while medium and high doses reduced MYOM3 fragment levels 5 fold and 8 fold, respectively. Due to the low inter-individual variability, measurement of the MYOM3 fragments enabled nearly all groups of mice to be distinguished with either of the thresholds (P-values <0.01 or 0.05) at the majority of time points (FIGS. 18E, F). Furthermore, MYOM3 fragment abundance was better correlated ($R^2=0.71$) with muscle force as measured by the escape test compared with CK ($R^2=0.59$) (FIG. 19).

Comparison of MYOM3 fragments with 3 other assays (biopsy, restoration of physical force, and CK) in models of 2 different muscular dystrophies, mdx (dystrophin deficient) and KO-Sgca (α-sarcoglycan deficient), demonstrated the superiority of MYOM3 fragments for the follow-up of gene therapy treatments relative to other assays. The advantages of the MYOM3 fragments compared to CK are their lower inter-individual variability between the patients of the same age, better correlation with the reconstitution of the dystrophin associated protein complex and muscle force restoration. The critical advantages of the MYOM3 fragments compared to the histological analysis of biopsies are that they are less invasive and provide information concerning body-wide muscle integrity. MYOM3 was the most efficient biomarker for distinguishing the 5 groups of KO-Sgca mice treated with different doses of rAAV vector. Taken together, our data demonstrate that MYOM3 fragments are excellent biomarkers for monitoring therapeutic outcomes in DMD and other muscular dystrophy patients.

Differential Expression of Different Myomesin Proteins May be Monitored to Study the Status of Different Types of Muscle Fibres.

Differential expression of different myomesins in muscle fibres (MYOM3 was found mainly in intermediate speed fibres (type IIa) of skeletal muscle, while fast fibres express more MYOM2 and MYOM1 is expressed in all muscle fibres (Schoenauer et al, 2008)) implies a possibility to follow the results of therapeutic treatment for each type of muscle fibres. We have found that after physical exercises fragments of myom2 and myom3 appeared in the bloodstream of mdx mice at different time, peaking at 1 and 2 days after exercise respectively (FIG. 21 and FIG. 16). This corresponds to the fact that fast muscles, rich in myom2, are preferentially affected in Duchenne muscular dystrophy (Webster, 1988).

REFERENCES

Bartoli M, Poupiot J, Goyenvalle A, Perez N, Garcia L, Danos O, Richard I. Noninvasive monitoring of therapeutic gene transfer in animal models of muscular dystrophies. Gene Ther. 2006 January; 13(1):20-8.

Betts C, Saleh A F, Arzumanov A A, Hammond S M, Godfrey C, Coursindel T, Gait M J, Wood M J (2012) Pip6-PMO, A New Generation of Peptide-oligonucleotide Conjugates With Improved Cardiac Exon Skipping Activity for DMD Treatment. *Molecular therapy Nucleic acids* 1: e38

Boisgerault F, Gross D A, Ferrand M, Poupiot J, Darocha S, Richard I, Galy A (2013) Prolonged gene expression in muscle is achieved without active immune tolerance using microRNA 142.3p-regulated rAAV gene transfer. *Human gene therapy* 24: 393-405

Brown B D, Venneri M A, Zingale A, Sergi Sergi L, Naldini L. Endogenous microRNA regulation suppresses transgene expression in hematopoietic lineages and enables stable gene transfer. Nat Med. 2006 May; 12(5):585-91. Epub 2006 Apr. 23.

Brussee V, Tardif F, Tremblay J P (1997) Muscle fibers of mdx mice are more vulnerable to exercise than those of normal mice. *Neuromuscular disorders: NMD* 7: 487-492

Carlson C G. A noninvasive procedure to detect muscle weakness in the mdx mouse. Muscle Nerve. 1990 June; 13(6):480-4.

Carlson C G, Rutter J, Bledsoe C, Singh R, Hoff H, Bruemmer K, Sesti J, Gatti F, Berge J, McCarthy L (2010) A simple protocol for assessing inter-trial and inter-examiner reliability for two noninvasive measures of limb muscle strength. *Journal of neuroscience methods* 186: 226-230

Chapman V M, Miller D R, Armstrong D, Caskey C T. Recovery of induced mutations for X chromosome-linked muscular dystrophy in mice. Proc Natl Acad Sci USA. 1989 February; 86(4): 1292-6.

Cullen M J, Jaros E (1988) Ultrastructure of the skeletal muscle in the X chromosome-linked dystrophic (mdx) mouse. Comparison with Duchenne muscular dystrophy. *Acta neuropathologica* 77: 69-81

Duclos F, Straub V, Moore S A, Venzke D P, Hrstka R F, Crosbie R H, Durbeej M, Lebakken C S, Ettinger A J, van der Meulen J, Holt K H, Lim L E, Sanes J R, Davidson B L, Faulkner J A, Williamson R, Campbell K P. Progressive muscular dystrophy in alpha-sarcoglycan-deficient mice. J Cell Biol. 1998 Sep. 21; 142(6):1461-71.

Duguez S, Duddy W, Johnston H, Laine J, Le Bihan M C, Brown K J, Bigot A, Hathout Y, Butler-Browne G, Partridge T (2013) Dystrophin deficiency leads to disturbance of LAMP1-vesicle-associated protein secretion. *Cellular and molecular life sciences: CMLS* 70: 2159-2174

Fougerousse F, Bartoli M, Poupiot J, Arandel L, Durand M, Guerchet N, Gicquel E, Danos O, Richard I (2007) Phenotypic correction of alpha-sarcoglycan deficiency by intra-arterial injection of a muscle-specific serotype 1 rAAV vector. *Molecular therapy: the journal of the American Society of Gene Therapy* 15: 53-61

Gasper M C, Gilchrist J M (2005) Creatine kinase: a review of its use in the diagnosis of muscle disease. *Medicine and health, Rhode Island* 88: 398, 400-394

Hack A A, Ly C T, Jiang F, Clendenin C J, Sigrist K S, Wollmann R L, McNally E M. Gamma-sarcoglycan deficiency leads to muscle membrane defects and apoptosis independent of dystrophin. J Cell Biol. 1998 Sep. 7; 142(5):1279-87.

Jearawiriyapaisam N, Moulton H M, Sazani P, Kole R, Willis M S (2010) Long-term improvement in mdx cardiomyopathy after therapy with peptide-conjugated morpholino oligomers. *Cardiovascular research* 85: 444-453

Kobayashi Y M, Rader E P, Crawford R W, Campbell K P (2012) Endpoint measures in the mdx mouse relevant for muscular dystrophy pre-clinical studies. *Neuromuscular disorders: NMD* 22: 34-42

Kornegay J N, Bogan J R, Bogan D J, Childers M K, Li J, Nghiem P, Detwiler D A, Larsen C A, Grange R W, Bhavaraju-Sanka R K, Tou S, Keene B P, Howard J F, Jr., Wang J, Fan Z, Schatzberg S J, Styner M A, Flanigan K M, Xiao X, Hoffman E P (2012) Canine models of Duchenne muscular dystrophy and their use in therapeutic strategies. *Mammalian genome: official journal of the International Mammalian Genome Society* 23: 85-108

Laure L, Suel L, Roudaut C, Bourg N, Ouali A, Bartoli M, Richard I, Danièle N. Cardiac ankyrin repeat protein is a marker of skeletal muscle pathological remodelling. FEBS J. 2009 February; 276(3):669-84.

Lostal W, Bartoli M, Bourg N, Roudaut C, Bentaïb A, Miyake K, Guerchet N, Fougerousse F, McNeil P, Richard I. Efficient recovery of dysferlin deficiency by dual adeno-associated vector-mediated gene transfer. Hum Mol Genet. 2010 May 15; 19(10):1897-907.

McArdle A, Edwards R H, Jackson M J (1994) Time course of changes in plasma membrane permeability in the dystrophin-deficient mdx mouse. *Muscle & nerve* 17: 1378-1384

McKeran R O, Halliday D, Purkiss P (1977) Increased myofibrillar protein catabolism in Duchenne muscular dystrophy measured by 3-methylhistidine excretion in the urine. *Journal of neurology, neurosurgery, and psychiatry* 40: 979-981

Moat S J, Bradley D M, Salmon R, Clarke A, Hartley L (2013) Newborn bloodspot screening for Duchenne muscular dystrophy: 21 years experience in Wales (UK). *European journal of human genetics: EJHG* 21: 1049-1053

Mussini E, Cornelio F, Colombo L, De Ponte G, Giudici G, Cotellessa L, Marcucci F (1984) Increased myofibrillar protein catabolism in duchenne muscular dystrophy measured by 3-methylhistidine excretion in the urine. *Muscle & nerve* 7: 388-391

Richard I, Roudaut C, Marchand S, Baghdiguian S, Herasse M, Stockholm D, Ono Y, Suel L, Bourg N, Sorimachi H, Lefranc G, Fardeau M, Sebille A, Beckmann J S (2000) Loss of calpain 3 proteolytic activity leads to muscular dystrophy and to apoptosis-associated IkappaBalpha/nuclear factor kappaB pathway perturbation in mice. *The Journal of cell biology* 151: 1583-1590

Roberts T C, Blomberg K E, McClorey G, El Andaloussi S, Godfrey C, Betts C, Coursindel T, Gait M J, Smith C I, Wood M J (2012) Expression analysis in multiple muscle groups and serum reveals complexity in the microRNA transcriptome of the mdx mouse with implications for therapy. *Molecular therapy Nucleic acids* 1: e39

Schoenauer R, Lange S, Hirschy A, Ehler E, Perriard J C, Agarkova I (2008) Myomesin 3, a novel structural component of the M-band in striated muscle. *Journal of molecular biology* 376: 338-351

Smith R H, Levy J R, Kotin R M (2009) A simplified baculovirus-AAV expression vector system coupled with one-step affinity purification yields high-titer rAAV stocks from insect cells. *Molecular therapy: the journal of the American Society of Gene Therapy* 17: 1888-1896

Snyder R O., et al. (1997). Persistent and therapeutic concentrations of human factor IX in mice after hepatic gene transfer of recombinant AAV vectors. Nat Genet. 16: 270-276.

Vilquin J T, Brussee V, Asselin I, Kinoshita I, Gingras M, Tremblay J P (1998) Evidence of mdx mouse skeletal muscle fragility in vivo by eccentric running exercise. *Muscle & nerve* 21: 567-576

Webster C, Silberstein L, Hays A P, Blau H M (1988) Fast muscle fibers are preferentially affected in Duchenne muscular dystrophy. *Cell* 52: 503-513

Wokke B H, Bos C, Reijnierse M, van Rijswijk C S, Eggers H, Webb A, Verschuuren J J, Kan H E (2013) Comparison of dixon and T1-weighted. MR methods to assess the degree of fat infiltration in duchenne muscular dystrophy patients. *Journal of magnetic resonance imaging: JMRI* 38: 619-624

Wooddell C I, Zhang G, Griffin J B, Hegge J O, Huss T, Wolff J A (2010) Use of Evans blue dye to compare limb muscles in exercised young and old mdx mice. *Muscle & nerve* 41: 487-499

Yin H, Saleh A F, Betts C, Camelliti P, Seow Y, Ashraf S, Arzumanov A, Hammond S, Merritt T, Gait M J, Wood M J (2011) Pip5 transduction peptides direct high efficiency oligonucleotide-mediated dystrophin exon skipping in heart and phenotypic correction in mdx mice. *Molecular therapy: the journal of the American Society of Gene Therapy* 19: 1295-1303

The invention claimed is:

1. A method for detecting myomesin 2 protein or myomesin 3 protein in a biological fluid from a subject comprising detecting the presence or absence of myomesin 2 protein or myomesin 3 protein in a sample of biological fluid of said subject, said detecting comprising:
   a) contacting said sample of biological fluid with antibodies that bind to an epitope of myomesin 2 or myomesin 3 and detecting the binding of said antibodies to said epitope; or
   b) specifically quantifying myomesin 2 protein or myomesin 3 protein in said sample of biological fluid by mass spectroscopy,
wherein the biological fluid is blood, serum, plasma, saliva or urine.

2. The method according to claim 1, said method comprising:
   measuring the level of the myomesin 2 protein or myomesin 3 protein in a biological fluid sample of the subject, and comparing this level to the level of said myomesin 2 protein or myomesin 3 protein in a biological fluid sample previously collected from the same subject.

3. The method according to claim 2, comprising:
   a) determining a reference level of the myomesin 2 protein or myomesin 3 protein by measuring the level of said myomesin 2 protein or myomesin 3 protein in a biological fluid sample of the subject; and
   b) determining a test level of myomesin 2 protein or myomesin 3 protein by measuring the level of said myomesin 2 protein or myomesin 3 protein in a second biological fluid sample collected from the same subject at a time after administration of a treatment.

4. The method according to claim 2, said method comprising treating a subject having muscular dystrophy and measuring the level of the myomesin 2 protein or myomesin 3 protein in a biological fluid sample of the subject after the treatment and comparing the level of the myomesin 2 protein or myomesin 3 protein after the treatment to the level of said myomesin 2 protein or said myomesin 3 protein in a biological fluid sample previously collected from the same subject prior to treatment.

5. The method according to claim 1, wherein the biological fluid is serum.

6. The method according to claim 1, said method comprising detecting the presence or absence of one or more polypeptide fragments of myomesin 3 in a sample of biological fluid of said subject, said one or more polypeptide fragments being a fragment of amino acids 350 to 1350 of SEQ ID NO: 1, said detecting comprising:
   a) contacting said sample of biological fluid with antibodies that bind to an epitope of said one or more fragments and detecting the binding of said antibodies to said epitope; or
   b) specifically quantifying said one or more fragments in said sample of biological fluid by mass spectroscopy.

7. The method according to claim 6, wherein the one or more fragments of myomesin 3 protein is selected from SEQ ID NO:2 to SEQ ID NO:16.

8. The method according to claim 1, comprising detecting the presence or absence of one or more C-terminal fragments of myomesin 3 protein, in a sample of biological fluid of said subject, said detecting comprising:
   a) contacting said sample of biological fluid with antibodies that bind to an epitope of said one or more C-terminal fragments and detecting the binding of said antibodies to said epitope; or
   b) specifically quantifying said one or more C-terminal fragments in said sample of biological fluid by mass spectroscopy,
wherein the biological fluid is blood, serum, plasma, saliva or urine.

9. The method according to claim 8, wherein the one or more C-terminal fragments of myomesin 3 protein is a fragment of about 110 or 140 kDa.

10. The method according to claim 1, wherein the biological fluid is obtained from a subject having a family history of a muscular dystrophy.

11. The method according to claim 1, wherein the biological fluid is obtained from a subject having a muscular dystrophy.

12. The method according to claim 1, wherein the biological fluid is obtained from a subject having undergone genome analysis and having been identified as having a predisposition to a muscular dystrophy on the basis of the genome analysis.

* * * * *

UNITED STATES PATENT AND TRADEMARK OFFICE
CERTIFICATE OF CORRECTION

PATENT NO.         : 11,099,193 B2
APPLICATION NO.    : 15/110868
DATED              : August 24, 2021
INVENTOR(S)        : Jeremy Rouillon et al.

Page 1 of 1

It is certified that error appears in the above-identified patent and that said Letters Patent is hereby corrected as shown below:

In the Specification

Column 18,
Lines 20-21, "RXRRBRRXRYQMRXRBRXRB" should read
--RXRRBRRXRYQFLIRXRBRXRB--.

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*